US010151819B2

(12) United States Patent
Choi et al.

(10) Patent No.: US 10,151,819 B2
(45) Date of Patent: Dec. 11, 2018

(54) MAGNETIC RESONANCE IMAGING APPARATUS AND METHOD OF SCANNING BLOOD VESSEL

(71) Applicant: SAMSUNG ELECTRONICS CO., LTD., Suwon-si (KR)

(72) Inventors: Joon-sung Choi, Anyang-si (KR); Dae-ho Lee, Seongnam-si (KR); Sang-young Zho, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 331 days.

(21) Appl. No.: 15/227,359

(22) Filed: Aug. 3, 2016

(65) Prior Publication Data

US 2017/0082715 A1 Mar. 23, 2017

(30) Foreign Application Priority Data

Sep. 18, 2015 (KR) .................. 10-2015-0132609

(51) Int. Cl.
*G01R 33/561* (2006.01)
*G01R 33/563* (2006.01)
*A61B 5/02* (2006.01)
*A61B 5/026* (2006.01)
(Continued)

(52) U.S. Cl.
CPC .......... *G01R 33/5635* (2013.01); *A61B 5/026* (2013.01); *A61B 5/02007* (2013.01);
(Continued)

(58) Field of Classification Search
CPC .......... G01R 33/5635; G01R 33/56308; A61B 5/0555
See application file for complete search history.

(56) References Cited

U.S. PATENT DOCUMENTS 5,167,232 A 12/1992 Parker et al.
5,225,779 A * 7/1993 Parker .................. G01R 33/563
324/306

(Continued)

FOREIGN PATENT DOCUMENTS

EP 0803739 A1 10/1997
JP 7-265277 A 10/1995
(Continued)

OTHER PUBLICATIONS

Communication dated May 15, 2017, from the European Patent Office in counterpart European Application No. 16187053.0.
(Continued)

*Primary Examiner* — Giovanni Astacio-Oquendo
*Assistant Examiner* — Alvaro Fortich
(74) *Attorney, Agent, or Firm* — Sughrue Mion, PLLC

(57) ABSTRACT

A method, which is performed by an MRI apparatus, of scanning a blood vessel, includes: sequentially applying, according to a time-of-flight (TOF) method, radio frequency (RF) pulses respectively to first grouped slabs during a first repetition time (TR); sequentially acquiring MR signals respectively corresponding to the RF pulses applied during the first TR; sequentially applying, according to the TOF method, RF pulses respectively to second grouped slabs during a second TR; and sequentially acquiring MR signals respectively corresponding to the RF pulses applied during the second TR.

19 Claims, 17 Drawing Sheets

(51) Int. Cl.
*A61B 5/055* (2006.01)
*G01R 33/483* (2006.01)

(52) U.S. Cl.
CPC .......... *A61B 5/0555* (2013.01); *G01R 33/561* (2013.01); *G01R 33/56308* (2013.01); *G01R 33/4835* (2013.01); *G01R 33/4838* (2013.01)

(56) References Cited

U.S. PATENT DOCUMENTS

| | | | |
|---|---|---|---|
| 6,456,073 B2 | 9/2002 | Uetake et al. | |
| 6,814,280 B2 * | 11/2004 | Miyoshi | G01R 33/56308 324/318 |
| 7,898,253 B2 * | 3/2011 | Dai | G01R 33/5635 324/307 |
| 9,523,754 B2 | 12/2016 | Park et al. | |
| 2003/0160611 A1 | 8/2003 | Miyoshi et al. | |
| 2009/0161934 A1 | 6/2009 | Zhao | |
| 2014/0152308 A1 | 6/2014 | Lee et al. | |
| 2015/0131884 A1 | 5/2015 | Kimura | |

FOREIGN PATENT DOCUMENTS

| | | |
|---|---|---|
| JP | 2003-250775 A | 9/2003 |
| JP | 201418571 A | 2/2014 |
| JP | 201523909 A | 2/2015 |
| JP | 2015116474 A | 6/2015 |
| KR | 1020100103533 A | 9/2010 |
| KR | 101486777 B1 | 1/2015 |
| KR | 10-2015-0048312 A | 5/2015 |

OTHER PUBLICATIONS

Communication dated Oct. 5, 2016, issued by the Korean Intellectual Property Office in counterpart Korean Patent Application No. 10-2015-132609.

Communication dated Feb. 1, 2017, issued by the Korean Intellectual Property Office in counterpart Korean Application No. 10-2015-0132609.

* cited by examiner

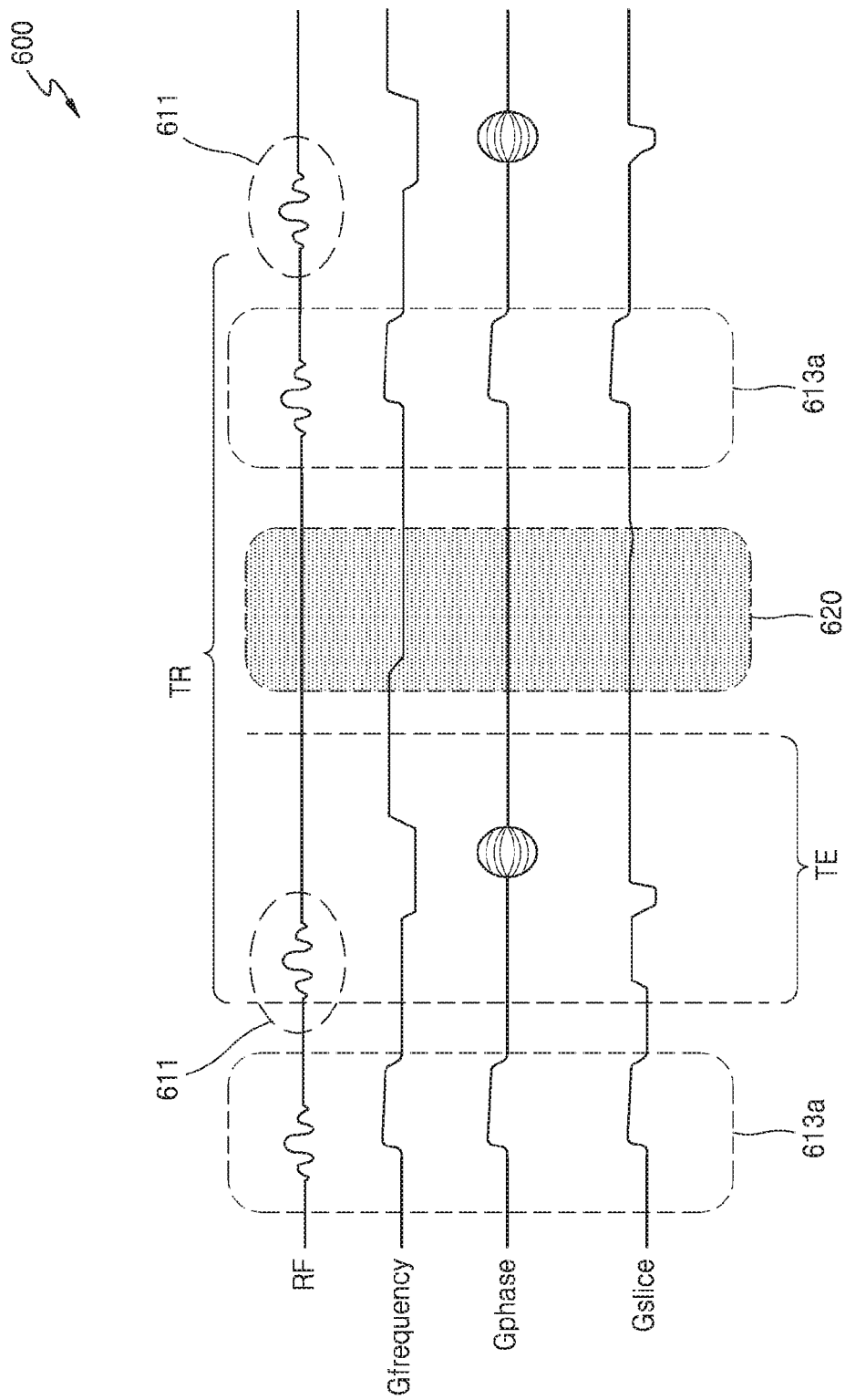

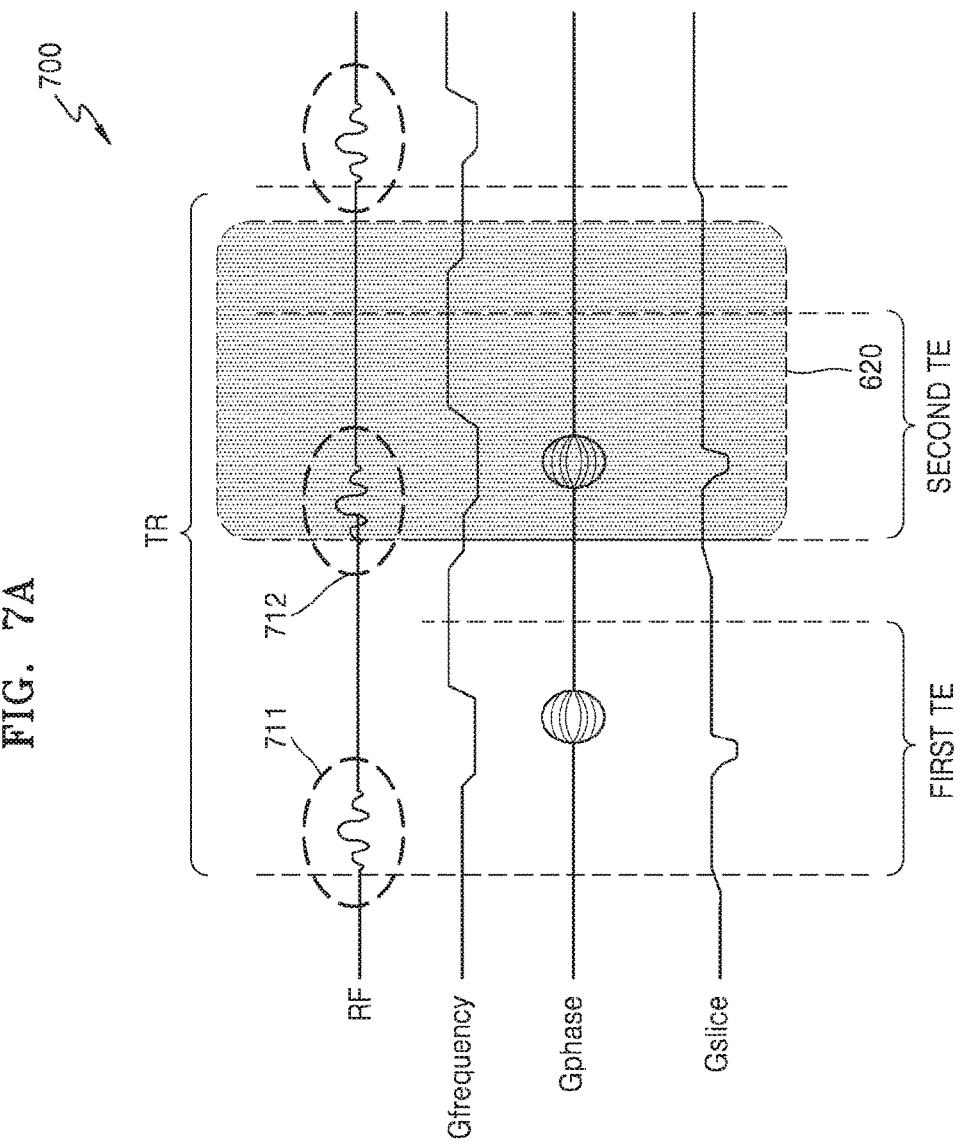

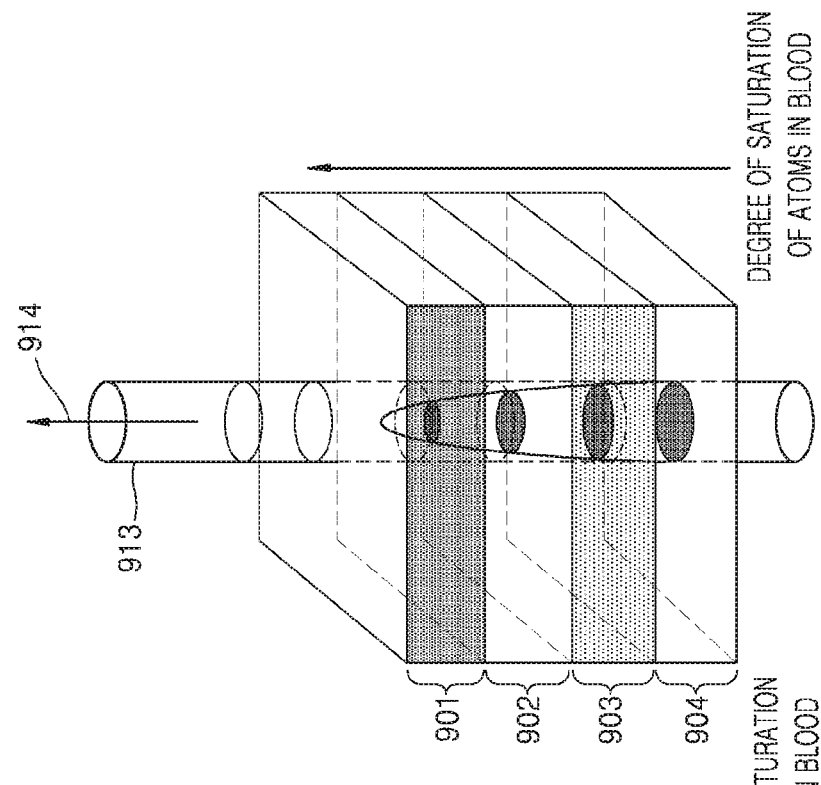
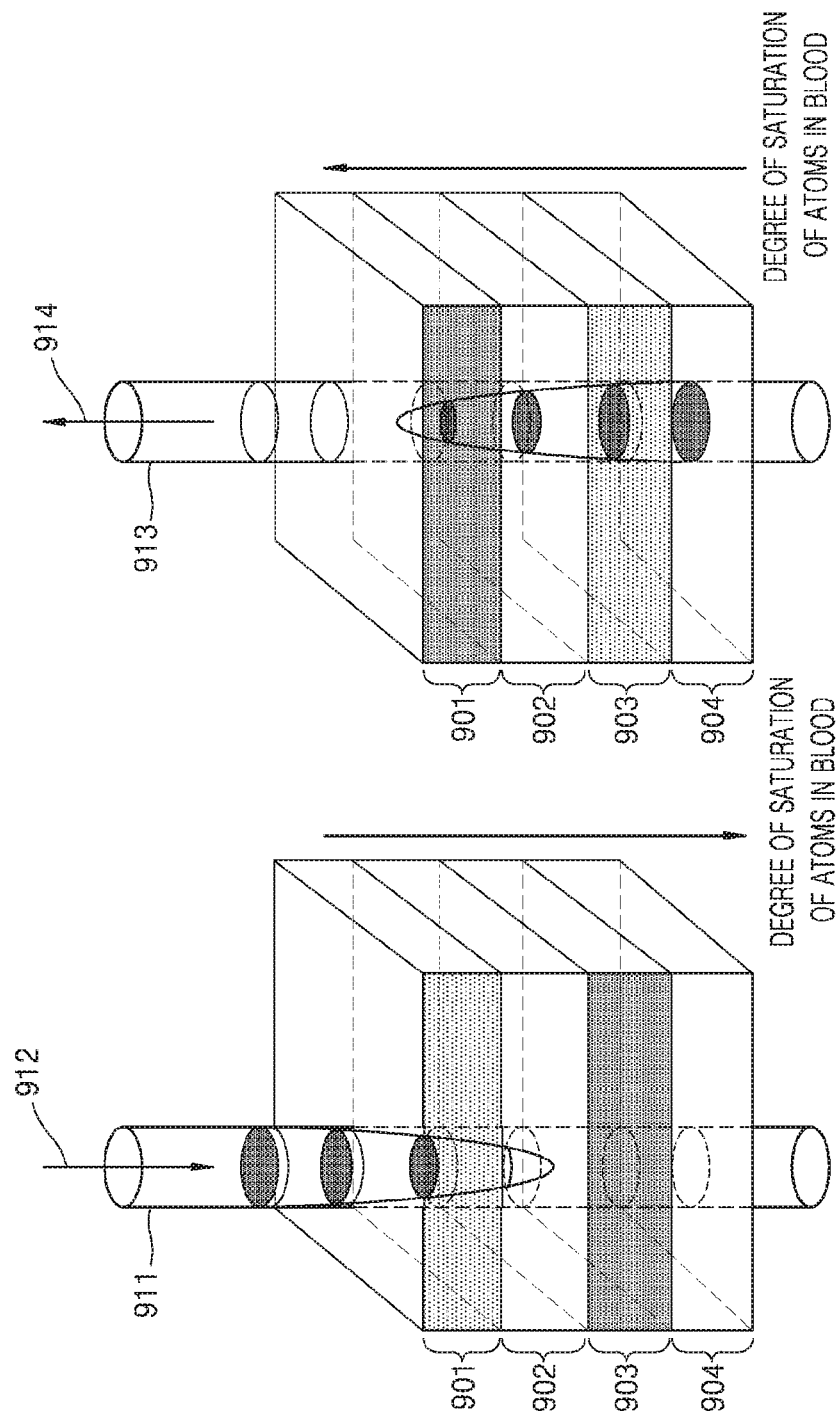

MAGNETIC RESONANCE IMAGING APPARATUS AND METHOD OF SCANNING BLOOD VESSEL

CROSS-REFERENCE TO RELATED APPLICATION

This application claims priority from Korean Patent Application No. 10-2015-0132609, filed on Sep. 18, 2015, in the Korean Intellectual Property Office, the disclosure of which is incorporated herein in its entirety by reference.

BACKGROUND

1. Field

Apparatuses and methods consistent with exemplary embodiments relate to magnetic resonance imaging (MRI) of a blood vessel.

2. Description of the Related Art

An MRI apparatus uses a magnetic field to capture an image of an object. The MRI apparatus is widely used for the accurate diagnosis because stereoscopic images of bones, lumbar discs, joints, nerve ligaments, etc. can be obtained at desired angles.

The MRI apparatus is configured to acquire MR signals and reconstruct the acquired MR signals into an image to be output. Specifically, the MRI apparatus acquires MR signals by using a radio frequency (RF) multi-coil including RF coils, a permanent magnet, and gradient coils.

In detail, RF signals generated using a pulse sequence for generating RF signals may be applied to an object via the RF multi-coil, and MR images may be reconstructed by sampling MR signals corresponding to the applied RF signals.

In a related art MRI, an average scan time is about 1 hour. Most MRI apparatuses include an elongated, narrow bore. A patient who is to undergo MRI is placed inside the bore and needs to remain substantially motionless during the scanning process. Thus, the patients having a serious medical condition or having a fear of enclosed spaces (claustrophobia) have difficulty undergoing an MRI scan, and most patients may feel bored and uncomfortable because of a long scan time.

Thus, there is an increasing need to provide an MRI apparatus and method which are capable of reconstructing a high contrast MR image while shortening an MRI scan time.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments may provide MRI apparatuses and methods of scanning a blood vessel, which are capable of reconstructing a high contrast MR image while shortening an MRI scan time.

According to an aspect of an exemplary embodiment, a method, performed by an MRI apparatus, of scanning a blood vessel includes: sequentially applying, according to a time-of-flight (TOF) method, a plurality of RF pulses respectively to a plurality of interleaved first group slabs among a plurality of slabs during a first repetition time (TR); sequentially acquiring a plurality of MR signals respectively corresponding to the plurality of RF pulses applied during the first TR; sequentially applying, according to the TOF method, a plurality of RF pulses respectively to a plurality of interleaved second group slabs among the plurality of slabs during a second TR; and sequentially acquiring a plurality of MR signals respectively corresponding to the plurality of RF pulses applied during the second TR.

The plurality of slabs may include first through fourth slabs that are sequentially arranged. The interleaved first group slabs may include the first and third slabs, and the interleaved second group slabs may include the second and fourth slabs.

The sequential applying of the plurality of RF pulses respectively to the interleaved first group slabs may include: generating a first flip angle schedule corresponding to the first and third slabs based on at least one of a direction and a velocity of blood flow; and adjusting, based on the generated first flip angle schedule, a flip angle of a first RF pulse corresponding to the first slab and a flip angle of a third RF pulse corresponding to the third slab.

The generating of the first flip angle schedule may include: generating, according to blood flowing into the first slab, the first flip angle schedule having a slope that increases at a predetermined rate; and generating, according to the blood flowing into the fourth slab, the first flip angle schedule having a slope that decreases at a predetermined rate.

The sequential applying of the plurality of RF pulses respectively to the interleaved second group slabs may include: generating a second flip angle schedule corresponding to the second and fourth slabs based on at least one of a direction and a velocity of blood flow; and adjusting, based on the generated second flip angle schedule, a flip angle of a second RF pulse corresponding to the second slab and a flip angle of a fourth RF pulse corresponding to the fourth slab.

The generating of the second flip angle schedule may include: generating, according to blood flowing into the first slab, the second flip angle schedule having a slope that increases at a predetermined rate, and generating, according to the blood flowing into the fourth slab, the second flip angle schedule having a slope that decreases at a predetermined rate.

The method may further include applying saturation RF pulses.

The plurality of RF pulses may be applied based on a three-dimensional (3D) TOF method.

The method may further include reconstructing a 3D image of the blood vessel based on the plurality of MR signals acquired during the first and second TRs.

According to an aspect of an exemplary embodiment, an MRI apparatus includes: an RF controller configured to sequentially apply, according to a TOF method, a plurality of RF pulses respectively to a plurality of interleaved first group slabs among a plurality of slabs during a first repetition time (TR); and a signal transceiver configured to sequentially acquire a plurality of MR signals respectively corresponding to the plurality of RF pulses applied during the first TR. The RF controller sequentially applies, according to the TOF method, a plurality of RF pulses respectively to a plurality of interleaved second group slabs among the plurality of slabs during a second TR, and the signal transceiver sequentially acquires a plurality of MR signals respectively corresponding to the plurality of RF pulses applied during the second TR.

The plurality of slabs may include first through fourth slabs that are sequentially arranged. The interleaved first group slabs may include the first and third slabs, and the interleaved second group slabs may include the second and fourth slabs.

The RF controller is further configured to generate a first flip angle schedule corresponding to the first and third slabs based on at least one of a direction and a velocity of blood flow and to adjust, based on the generated first flip angle schedule, a flip angle of a first RF pulse corresponding to the first slab and a flip angle of a third RF pulse corresponding to the third slab.

The RF controller is further configured to generate, according to blood flowing into the first slab, the first flip angle schedule having a slope that increases at a predetermined rate and to generate, according to the blood flowing into the third slab, the first flip angle schedule having a slope that decreases at a predetermined rate.

The RF controller is further configured to generate a second flip angle schedule corresponding to the second and fourth slabs based on at least one of a direction and a velocity of blood flow and to adjust, based on the generated second flip angle schedule, a flip angle of a second RF pulse corresponding to the second slab and a flip angle of a fourth RF pulse corresponding to the fourth slab.

The RF controller is further configured to generate, according to blood flowing into the second slab, the second flip angle schedule having a slope that increases at a predetermined rate and to generate, according to the blood flowing into the fourth slab, the second flip angle schedule having a slope that decreases at a predetermined rate.

The RF controller is further configured to apply saturation RF pulses.

The RF controller is further configured to apply the plurality of RF pulses based on a 3D TOF method.

The MRI apparatus may further include an image processor configured to reconstruct a 3D image of a blood vessel based on the plurality of MR signals acquired during the first and second TRs.

According to an aspect of an exemplary embodiment, a non-transitory computer-readable recording medium has recorded thereon a program for performing the method of scanning a blood vessel on a computer.

BRIEF DESCRIPTION OF THE DRAWINGS

The above and/or other aspects will become more apparent by describing certain exemplary embodiments with reference to the accompanying drawings, in which:

FIG. 6A is a diagram for explaining a method of an MRI apparatus based on a 3D TOF technique;

FIG. 7A is another diagram for explaining a method of operating an MRI apparatus according to a 3D TOF technique;

FIGS. 9A and 9B are diagrams for explaining a direction of a blood flow and a saturated state of atoms in the blood;

DETAILED DESCRIPTION

Figure 1:
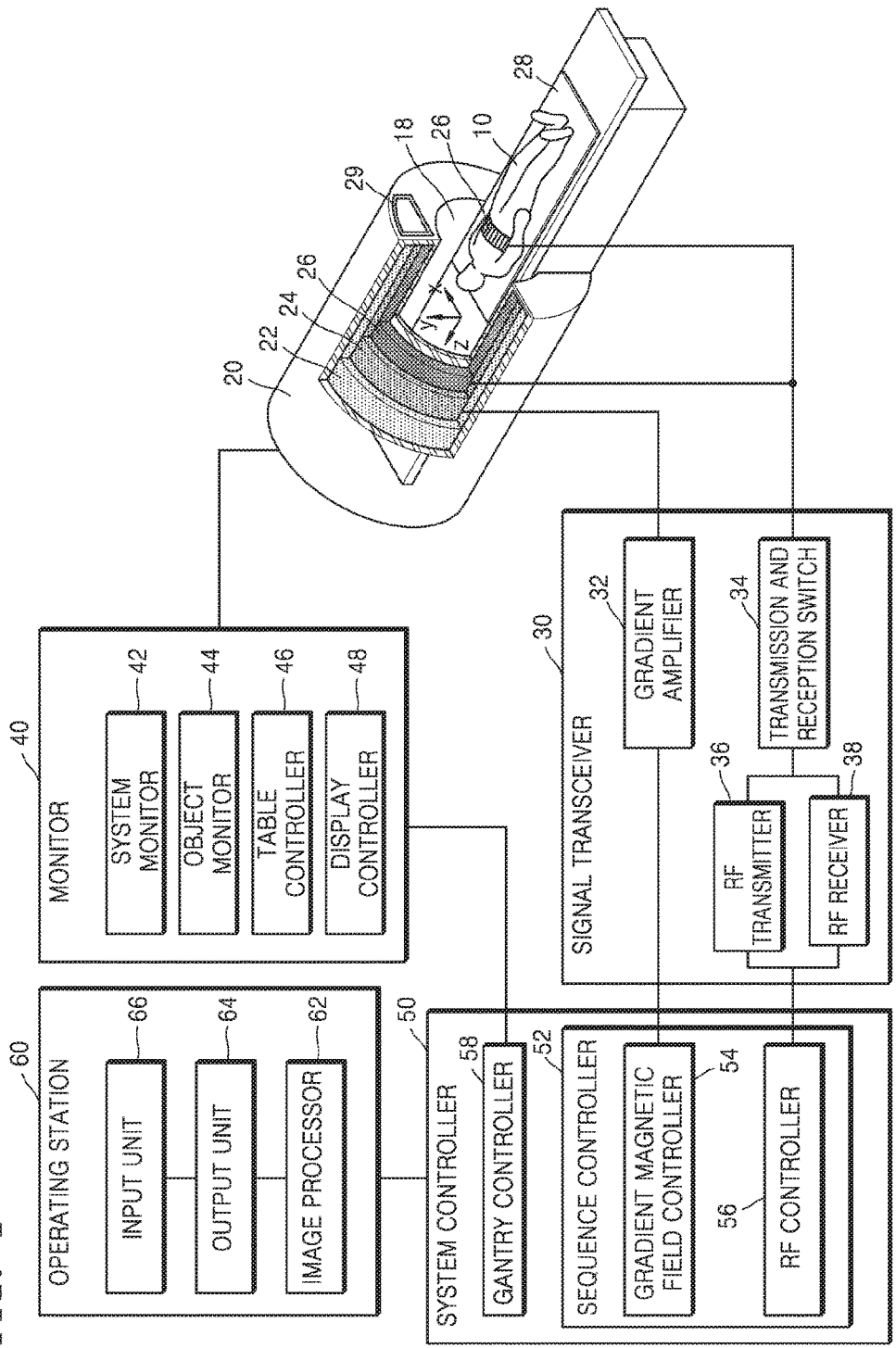
FIG. 1 is a block diagram of an MRI system.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

The terms used in this specification are those general terms currently widely used in the art in consideration of functions regarding the present disclosure, but the terms may vary according to the intention of those of ordinary skill in the art, precedents, or new technology in the art. Also, some terms may be arbitrarily selected by the applicant, and the meaning of the selected terms will be described in detail in the detailed description of the present specification. Thus, the terms used herein have to be defined based on the meaning of the terms together with the description throughout the specification.

It will be understood that, although the terms "first", "second", etc. may be used herein to describe various elements and/or components, these elements and/or components should not be limited by these terms. These terms are only used to distinguish one element or component from another element or component. For example, a first element or component may be termed a second element or component or vice versa without departing from the teachings of exemplary embodiments. As used herein, the term "and/or" includes any and all combinations of one or more of the associated listed items. Expressions such as "at least one of," when preceding a list of elements, modify the entire list of elements and do not modify the individual elements of the list.

When a part "includes" or "comprises" an element, unless there is a particular description contrary thereto, the part can further include other elements, not excluding the other elements. Also, the term "unit" in the embodiments of the present invention means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Throughout the specification, an "image" may mean multi-dimensional data formed of discrete image elements, e.g., pixels in a two-dimensional (2D) image and voxels in a 3D image. For example, an image may be a medical image of an object acquired by an X-ray apparatus, a computed tomography (CT) apparatus, an MRI apparatus, an ultrasound diagnosis apparatus, or another medical imaging apparatus.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof. The object may be a phantom. The phantom means a material having a density, an effective atomic number, and a volume that are approximately the same as those of an organism. For example, the phantom may be a spherical phantom having properties similar to the human body.

Furthermore, in the present specification, an MRI refers to an image of an object obtained by using the nuclear magnetic resonance principle.

Furthermore, in the present specification, a "pulse sequence" refers to continuity of signals repeatedly applied by an MRI apparatus. The pulse sequence may include a time parameter of an RF pulse, for example, repetition time (TR) or echo time (TE).

Furthermore, in the present specification, a "pulse sequence schematic diagram" shows an order of events that occur in an MRI apparatus. For example, the pulse sequence schematic diagram may be a diagram showing an RF pulse, a gradient pulse, an MR signal, or the like according to time.

Furthermore, in the present specification, "TR" may be a time between repetitions of an RF pulse. For example, the TR may be defined as a time interval from a point of time when an RF pulse with a predetermined magnitude is transmitted to a point of time when an RF pulse with the same magnitude is transmitted again.

Furthermore, in the specification, "TE" may be defined as a time interval from a point of time when an RF pulse is transmitted to a point of time when its MR signal is acquired.

Furthermore, in the specification, "spatial encoding" may mean acquisition of spatial information along an axis (direction) of a magnetic field gradient by applying a linear gradient magnetic field that induces extra dephasing of proton spins, in addition to dephasing of proton spins caused by an RF signal.

An MRI apparatus is an apparatus for acquiring a sectional image of a part of an object by expressing, in a contrast comparison, a strength of a MR signal with respect to an RF signal generated in a magnetic field having a specific strength. For example, if an RF signal that only resonates a specific atomic nucleus (for example, a hydrogen atomic nucleus) is emitted for an instant toward the object placed in a strong magnetic field and then such emission stops, an MR signal is emitted from the specific atomic nucleus, and thus the MRI apparatus may receive the MR signal and acquire an MR image. The MR signal denotes an RF signal emitted from the object. An intensity of the MR signal may be determined according to a density of a predetermined atom (for example, hydrogen) of the object, a relaxation time T1, a relaxation time T2, and a flow of blood or the like.

MRI apparatuses include characteristics different from those of other imaging apparatuses. Unlike imaging apparatuses such as CT apparatuses that acquire images according to a direction of detection hardware, MRI apparatuses may acquire 2D images or 3D volume images that are oriented toward an optional point. MRI apparatuses do not expose humans to radiation, unlike CT apparatuses, X-ray apparatuses, position emission tomography (PET) apparatuses, and single photon emission CT (SPECT) apparatuses, may acquire images having high soft tissue contrast, and may acquire neurological images, intravascular images, musculoskeletal images, and oncologic images that are required to precisely capturing abnormal tissues.

FIG. 1 is a block diagram of an MRI system.

Referring to FIG. 1, the MRI system may include a gantry 20, a signal transceiver 30, a monitor 40, a system controller 50, i.e., a microprocessor, and an operating station 60.

The gantry 20 prevents external emission of electromagnetic waves generated by a main magnet 22, a gradient coil or coils 24, and an RF coil or coils 26. A magnetostatic field and a magnetic field gradient are formed in a bore 18 in the gantry 20, and an RF signal is emitted toward an object 10.

The main magnet 22, the gradient coil 24, and the RF coil 26 may be arranged in a predetermined direction of the gantry 20. The predetermined direction may be a coaxial cylinder direction. The object 10 may be disposed on a table 28 that is capable of being inserted into a cylinder along a horizontal axis of the cylinder.

The main magnet 22 generates a magnetostatic field or a static magnetic field for aligning magnetic dipole moments of atomic nuclei of the object 10 in a constant direction. A precise and accurate MR image of the object 10 may be obtained due to a magnetic field generated by the main magnet 22 being strong and uniform.

The gradient coil 24 includes X, Y, and Z coils for generating magnetic field gradients in X-, Y-, and Z-axis directions crossing each other at right angles. The gradient coil 24 may provide location information of each region of the object 10 by differently inducing resonance frequencies according to the regions of the object 10.

The RF coil 26 may emit an RF signal toward a patient and receive an MR signal emitted from the patient. In detail, the RF coil 26 may transmit, toward atomic nuclei and having precessional motion, an RF signal having the same frequency as that of the precessional motion to the patient, stop transmitting the RF signal, and then receive an MR signal emitted from the patient.

For example, in order to transit an atomic nucleus from a low energy state to a high energy state, the RF coil 26 may generate and apply an electromagnetic wave signal that is an RF signal corresponding to a type of the atomic nucleus, to the object 10. When the electromagnetic wave signal generated by the RF coil 26 is applied to the atomic nucleus, the atomic nucleus may transit from the low energy state to the high energy state. Then, when electromagnetic waves generated by the RF coil 26 disappear, the atomic nucleus to which the electromagnetic waves were applied transits from the high energy state to the low energy state, thereby emitting electromagnetic waves having a Larmor frequency. In other words, when the applying of the electromagnetic wave signal to the atomic nucleus is stopped, an energy level of the atomic nucleus is changed from a high energy level to a low energy level, and thus the atomic nucleus may emit electromagnetic waves having a Larmor frequency. The RF coil 26 may receive electromagnetic wave signals from atomic nuclei included in the object 10.

The RF coil 26 may be realized as one RF transmitting and receiving coil having both a function of generating electromagnetic waves each having an RF that corresponds to a type of an atomic nucleus and a function of receiving electromagnetic waves emitted from an atomic nucleus. Alternatively, the RF coil 26 may be realized as a transmission RF coil having a function of generating electromagnetic waves each having an RF that corresponds to a type of an atomic nucleus, and a reception RF coil having a function of receiving electromagnetic waves emitted from an atomic nucleus.

The RF coil 26 may be fixed to the gantry 20 or may be detachable. When the RF coil 26 is detachable, the RF coil 26 may be an RF coil for a part of the object, such as a head RF coil, a chest RF coil, a leg RF coil, a neck RF coil, a shoulder RF coil, a wrist RF coil, or an ankle RF coil.

The RF coil 26 may communicate with an external apparatus via wires and/or wirelessly, and may also perform dual tune communication according to a communication frequency band.

The RF coil 26 may be a birdcage coil, a surface coil, or a transverse electromagnetic (TEM) coil according to structures.

The RF coil 26 may be a transmission exclusive coil, a reception exclusive coil, or a transmission and reception coil according to methods of transmitting and receiving an RF signal.

The RF coil 26 may be an RF coil having various numbers of channels, such as 16 channels, 32 channels, 72 channels, and 144 channels.

Hereinafter, it is assumed that the RF coil 26 is an RF multi-coil including N coils respectively corresponding to a plurality of channels, i.e., first through N-th channels. In this case, the RF coil 26 may also be referred to as a multi-channel RF coil or an RF multi-coil.

The gantry 20 may further include a display 29 disposed outside the gantry 20 and a display (not shown) disposed inside the gantry 20. The gantry 20 may provide predetermined information to the user or the object 10 through the display 29 and the display respectively disposed outside and inside the gantry 20.

The signal transceiver 30 may control the gradient magnetic field formed inside the gantry 20, i.e., in the bore, according to a predetermined MR sequence, and control transmission and reception of an RF signal and an MR signal.

The signal transceiver 30 may include a gradient amplifier 32, a transmission and reception switch 34, an RF transmitter 36, and an RF receiver 38.

The gradient amplifier 32 drives the gradient coil 24 included in the gantry 20, and may supply a pulse signal for generating a gradient magnetic field to the gradient coil 24 under the control of a gradient magnetic field controller 54. By controlling the pulse signal supplied from the gradient amplifier 32 to the gradient coil 24, magnetic field gradients in X-, Y-, and Z-axis directions may be synthesized.

The RF transmitter 36 and the RF receiver 38 may drive the RF coil 26. The RF transmitter 36 may supply an RF pulse in a Larmor frequency to the RF coil 26, and the RF receiver 38 may receive an MR signal received by the RF coil 26.

The transmission and reception switch 34 may adjust transmitting and receiving directions of the RF signal and the MR signal. For example, the transmission and reception switch 34 may emit the RF signal toward the object 10 through the RF coil 26 during a transmission mode, and receive the MR signal from the object 10 through the RF coil 26 during a reception mode. The transmission and reception switch 34 may be controlled by a control signal output by an RF controller 56.

The monitor 40 may monitor or control the gantry 20 or devices mounted on the gantry 20. The monitor 40 may include a system monitor 42, an object monitor 44, a table controller 46, and a display controller 48.

The system monitor 42 may monitor and control a state of the magnetostatic field, a state of the gradient magnetic field, a state of the RF signal, a state of the RF coil 26, a state of the table 28, a state of a device measuring body information of the object 10, a power supply state, a state of a thermal exchanger, and a state of a compressor.

The object monitor 44 monitors a state of the object 10. In detail, the object monitor 44 may include a camera for observing a movement or position of the object 10, a respiration measurer for measuring the respiration of the object 10, an electrocardiogram (ECG) measurer for measuring the electrical activity of the object 10, or a temperature measurer for measuring a temperature of the object 10.

The table controller 46 controls a movement of the table 28 where the object 10 is positioned. The table controller 46 may control the movement of the table 28 according to a sequence control of a sequence controller 52. For example, during moving imaging of the object 10, the table controller 46 may continuously or discontinuously move the table 28 according to the sequence control of the sequence controller 52, and thus the object 10 may be photographed in a field of view (FOV) larger than that of the gantry 20.

The display controller 48 controls the display 29 disposed outside the gantry 20 and the display disposed inside the gantry 20. In detail, the display controller 48 may control the display 29 and the display to be on or off, and may control a screen image to be output on the display 29 and the display. Also, when a speaker is located inside or outside the gantry 20, the display controller 48 may control the speaker to be on or off, or may control sound to be output via the speaker.

The system controller 50 may include the sequence controller 52 for controlling a sequence of signals formed in the gantry 20, and a gantry controller 58 for controlling the gantry 20 and the devices mounted on the gantry 20.

The sequence controller 52 may include the gradient magnetic field controller 54 for controlling the gradient amplifier 32, and the RF controller 56 for controlling the RF transmitter 36, the RF receiver 38, and the transmission and reception switch 34. The sequence controller 52 may control the gradient amplifier 32, the RF transmitter 36, the RF receiver 38, and the transmission and reception switch 34 according to a pulse sequence received from the operating station 60. Here, the pulse sequence includes all information required to control the gradient amplifier 32, the RF transmitter 36, the RF receiver 38, and the transmission and reception switch 34. For example, the pulse sequence may include information about a strength, an application time, and application timing of a pulse signal applied to the gradient coil 24.

The operating station 60 may request the system controller 50 to transmit pulse sequence information while controlling an overall operation of the MRI system.

The operating station 60 may include an image processor 62 for receiving and processing the MR signal received by the RF receiver 38, an output unit 64, e.g., an output transmitter, and an input unit 66, e.g., an input receiver.

The image processor 62 may process the MR signal received from the RF receiver 38 so as to generate MR image data of the object 10.

The image processor 62 receives the MR signal received by the RF receiver 38 and performs any one of various signal processes, such as amplification, frequency transformation, phase detection, low frequency amplification, and filtering, on the received MR signal.

For example, the image processor 62 may arrange digital data in a k space of a memory, and rearrange the digital data into image data via 2D or 3D Fourier Transform.

The image processor 62 may perform a composition process or difference calculation process on image data if required. The composition process may include an addition process on a pixel or a maximum intensity projection (MIP) process. The image processor 62 may store not only the rearranged image data but also image data on which a composition process or a difference calculation process is performed, in a memory (not shown) or an external server.

The image processor 62 may perform any of the signal processes on the MR signal in parallel. For example, the image processor 62 may perform a signal process on a plurality of MR signals received by a multi-channel RF coil in parallel so as to rearrange the plurality of MR signals into image data.

The output unit 64 may output image data generated or rearranged by the image processor 62 to the user. The output unit 64 may also output information required for the user to manipulate the MRI system, such as a user interface (UI), user information, or object information. Examples of the output unit 64 may include a speaker, a printer, a cathode ray tube (CRT) display, a liquid crystal display (LCD), a plasma display panel (PDP), an organic light emitting diode (OLED) display, a field emission display (FED), an LED display, a vacuum fluorescent display (VFD), a digital light processing (DLP) display, a flat panel display, a 3D display, a transparent display, and other various appropriate output devices.

The user may input object information, parameter information, a scan condition, a pulse sequence, or information about image composition or difference calculation by using the input unit 66. The input unit 66 may be a keyboard, a mouse, a track ball, a voice recognizer, a gesture recognizer, a touch screen, or any other appropriate input devices.

The signal transceiver 30, the monitor 40, the system controller 50, and the operating station 60 are separate components in FIG. 1, but it will be obvious to one of ordinary skill in the art that respective functions of the signal transceiver 30, the monitor 40, the system controller 50, and the operating station 60 may be performed by another component. For example, the image processor 62 converts the MR signal received from the RF receiver 38 into a digital signal in FIG. 1, but alternatively, the conversion of the MR signal into the digital signal may be performed by the RF receiver 38 or the RF coil 26.

The gantry 20, the RF coil 26, the signal transceiver 30, the monitor 40, the system controller 50, and the operating station 60 may be connected to each other by wire or wirelessly, and when they are connected wirelessly, the MRI system may further include an apparatus (not shown) for synchronizing clock signals therebetween. Communication between the gantry 20, the RF coil 26, the signal transceiver 30, the monitor 40, the system controller 50, and the operating station 60 may be performed by using a high-speed digital interface, such as low voltage differential signaling (LVDS), asynchronous serial communication, such as a universal asynchronous receiver transmitter (UART), a low-delay network protocol, such as error synchronous serial communication or a controller area network (CAN), optical communication, or any other appropriate communication method.

Figure 2:
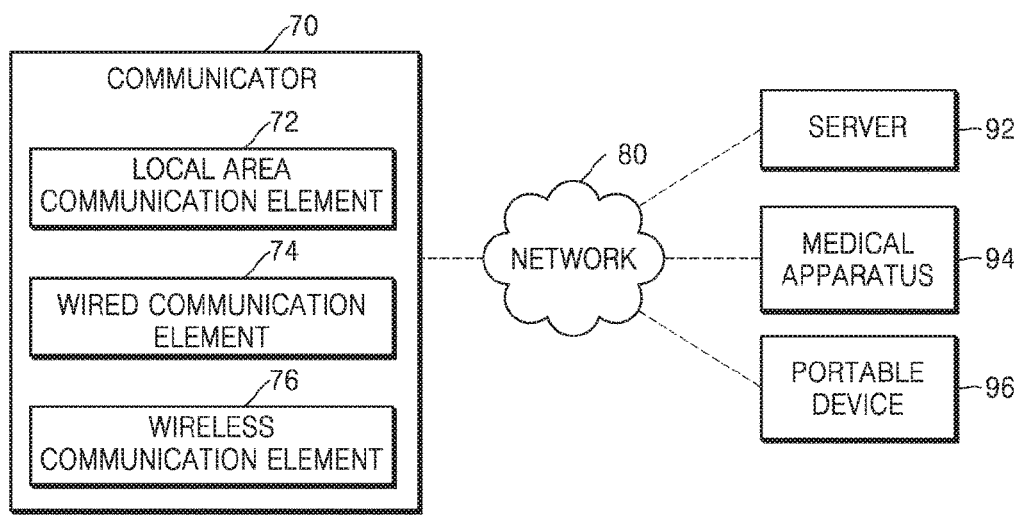
FIG. 2 illustrates a configuration of a communicator according to an exemplary embodiment.

FIG. 2 is a block diagram of a communicator 70 according to an exemplary embodiment. Referring to FIG. 2, the communicator 70 may be connected to at least one selected from the gantry 20, the signal transceiver 30, the monitor 40, the system controller 50, and the operating station 60 of FIG. 1.

The communicator 70 may transmit and receive data to and from a hospital server or another medical apparatus in a hospital, which is connected through a picture archiving and communication system (PACS), and perform data communication according to the digital imaging and communications in medicine (DICOM) standard.

As shown in FIG. 2, the communicator 70 may be connected to a network 80 by wire or wirelessly to communicate with a server 92, a medical apparatus 94, or a portable device 96.

In detail, the communicator 70 may transmit and receive data related to the diagnosis of an object through the network 80, and may also transmit and receive a medical image captured by the medical apparatus 94, such as a CT apparatus, an MRI apparatus, or an X-ray apparatus. In addition, the communicator 70 may receive a diagnosis history or a treatment schedule of the object from the server 92 and use the same to diagnose the object. The communicator 70 may perform data communication not only with the server 92 or the medical apparatus 94 in a hospital, but also with the portable device 96, such as a mobile phone, a personal digital assistant (PDA), or a laptop of a doctor or patient.

Also, the communicator 70 may transmit information about a malfunction of the MRI system or about a medical image quality to a user through the network 80, and receive a feedback regarding the information from the user.

The communicator 70 may include at least one component enabling communication with an external apparatus.

For example, the communicator 70 may include a local area communication element 72, a wired communication element 74, and a wireless communication element 76. The local area communication element 72 refers to a module for performing local area communication with an apparatus within a predetermined distance. Examples of local area communication technology according to an exemplary embodiment include, but are not limited to, a wireless local area network (LAN), Wi-Fi, Bluetooth, ZigBee, Wi-Fi direct (WFD), ultra wideband (UWB), infrared data association (IrDA), Bluetooth low energy (BLE), and near field communication (NFC).

The wired communication element 74 refers to a module for performing communication by using an electric signal or an optical signal. Examples of wired communication technology according to an exemplary include wired communication techniques using a pair cable, a coaxial cable, and an optical fiber cable, and other any appropriate wired communication technique.

The wireless communication element 76 transmits and receives a wireless signal to and from at least one selected from a base station, an external apparatus, and a server in a mobile communication network. Here, the wireless signal may be a voice call signal, a video call signal, or data in any one of various formats according to transmission and reception of a text/multimedia message.

Figure 3:
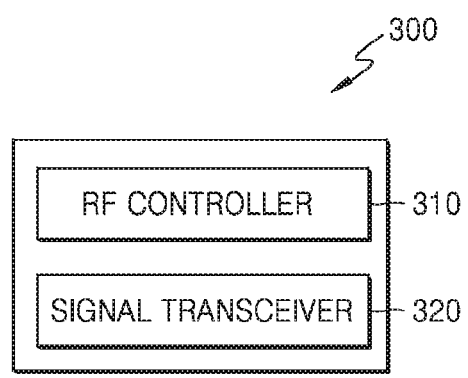
FIG. 3 is a block diagram of an MRI apparatus according to an exemplary embodiment.

FIG. 3 is a block diagram of an MRI apparatus 300 according to an exemplary embodiment.

The MRI apparatus 300 according to the exemplary embodiment may be any apparatus for reconstructing and/or processing an MR image. In detail, the MRI apparatus 300 may be an apparatus configured to apply RF pulses via a plurality of channel coils included in an RF multi-coil (not shown) to an object and generate an MR image by using MR signals acquired via the plurality of channel coils.

For example, the MRI apparatus 300 may be included in the MRI system described with reference to FIGS. 1 and 2. When the MRI apparatus 300 is included in the MRI system described with reference to FIG. 1, an RF controller 310 and a signal transceiver 320 illustrated in FIG. 3 may respectively correspond to the RF controller 56 and the signal transceiver 30 described with reference to FIG. 1. The RF multi-coil may correspond to the RF coil 26 described with reference to FIG. 1.

For example, the MRI apparatus 300 may be a server apparatus configured to provide a pulse sequence to be applied to an object, receive MR signals acquired by performing an MRI scan, and reconstruct an MR image by using the received MR signals. Here, the server apparatus may be a medical server apparatus placed in a hospital where a patient undergoes an MRI scan or in another hospital.

In detail, the MRI apparatus 300 may be the server 92, the medical apparatus 94, or the portable device 96 connected to the MRI system described with reference to FIGS. 1 and 2 to be operated, and may receive an MR signal acquired by the MRI system to reconstruct an MR image.

Referring to FIG. 3, the MRI apparatus 300 may include the RF controller 310 and the signal transceiver 320.

To acquire an MR image of an object, the RF controller 310 may control information about a signal strength (or signal intensity), application time, and application timing of an RF pulse that is applied via an RF multi-coil (not shown). Here, the RF multi-coil may correspond to the RF coil 26 in the MRI system described with reference to FIG. 1.

For example, the RF controller 310 may be connected to the operating station 60 described with reference to FIG. 1 and may receive an RF pulse sequence from the operating station 60. For example, the RF controller 310 may correspond to the RF controller 56 described with reference to FIG. 1.

The RF controller 310 may control a plurality of RF signals respectively corresponding to a plurality of slabs to be applied to the object. A slab may be a planar unit region having a predetermined thickness, from which data is acquired to reconstruct an MR image. In detail, the RF controller 310 may apply a plurality of RF pulses respectively corresponding to a plurality of slabs to an object, based on a 3D time of flight (TOF) method. A 3D TOF method is a technique for imaging blood vessels in the object and may be used to image protons flowing into a predetermined volume of the object by using flow-related enhancement or in-flow effect. In detail, in the 3D TOF method, after atoms in tissue of a predetermined volume of an object become saturated by a saturation pulse, as atoms in blood newly flowing into the predetermined volume (i.e., the atoms in blood not affected by a saturation pulse) are excited by an RF pulse, the atoms in the blood emit a signal having a greater strength than the atoms in the tissue. The 3D TOF method uses this phenomenon to image blood vessels. The 3D TOF method will be described in more detail below with reference to FIG. 5.

For example, the RF controller 310 may sequentially apply RF pulses respectively corresponding to a plurality of interleaved slabs to the object. For example, interleaving slabs means arranging the slabs at regular intervals, e.g., spatial distances in the object. For example, if first through fourth slabs are sequentially arranged in parallel to one another, the first and third slabs may be grouped, and the second and fourth slabs may be grouped, so that the first, second, third and fourth slabs are disposed to be interleaved with each other. The first through fourth slabs are positioned sequentially, but are not necessarily positioned adjacent one another in space. Also, the first through fourth slabs may be of the same thickness or of a different thickness.

Thus, the RF controller 310 mayسequentially apply different RF pulses respectively corresponding to different slabs to a plurality of interleaved slabs during one TR.

In detail, the RF controller 310 may group a plurality of slabs into a plurality of groups, each group including slabs interleaved with slabs of another group. For example, the RF controller 310 may repeatedly apply RF pulses respectively corresponding to a plurality of slabs in a first group to an object. Thereafter, the RF controller 310 may repeatedly apply RF pulses respectively corresponding to a plurality of slabs in a second group to the object.

Figure 4:
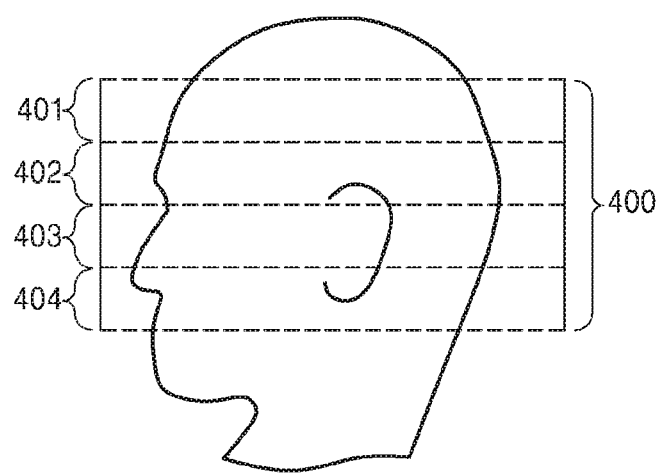
FIG. 4 illustrates an example in which an area being scanned is divided into slabs.

FIG. 4 illustrates an example in which an area 400 being scanned is divided into a plurality of slabs.

As shown in FIG. 4, the RF controller 310 may divide the area 400 being scanned into first through fourth slabs 401 through 404 arranged parallel to one another. For example, each of the first through fourth slabs 401 through 404 may be a volume region having a thickness of 5 centimeters (cm).

The RF controller 310 may group the first through fourth slabs 401 through 404 into two groups including interleaved slabs. For example, the RF controller 310 may group the first and third slabs 401 and 403 as a first group and the second and fourth slabs 402 and 404 as a second group. For example, the slabs in each group are not contiguous to each other, but are disposed to be spaced from each other at regular intervals in the area 400, i.e., in an interleaved manner. This arrangement may prevent the strength of acquired MR signals from decreasing by suppressing RF pulses that are being applied to an object from affecting adjacent slabs.

According to an exemplary embodiment, the RF controller 310 may sequentially apply first and third RF pulses, respectively corresponding to the first and third slabs 401 and 403 in the first group, to the object during each TR.

After the first and third RF pulses respectively corresponding to the first and third slabs 401 and 403 are applied to the object, the RF controller 310 may repeatedly apply second and fourth RF pulses, respectively corresponding to the second and fourth slabs 402 and 404 in the second group, to the object during each TR.

Referring back to FIG. 3, the MRI apparatus 300 may apply RF pulses respectively corresponding to grouped slabs during one TR, thereby reducing scan time required to scan a blood vessel.

For example, scan time may be determined by the number of slabs, TR, number of phase encoding operations, number of slice encoding operations, number of excitations (NEX) (or number of acquisitions), number of acquisitions of MR signals using phase encoding gradients having the same magnitude, etc. Here, the TR may be the time (e.g., 20 ms) from application of one RF pulse to application of the next RF pulse. In detail, the TR may include a specific time gap (e.g., 15 ms) needed even after a time point (e.g., 5 ms) when an MR signal corresponding to an applied RF pulse is acquired. This is because a certain amount of time is required to again excite atoms in a slab that have been previously excited by the RF pulse.

According to an exemplary embodiment, as described above, the RF controller 310 may apply a plurality of interleaved RF pulses to the object during one TR. In detail, after one RF pulse is applied, an RF pulse corresponding to another slab may be applied using the above-described specific time gap. Thus, according to an exemplary embodiment, the scan time may be reduced by a factor of the number of RF pulses being sequentially applied during one TR (i.e., the number of grouped slabs). For example, if the RF controller 310 applies two RF pulses during one TR as described with reference to FIG. 4, the scan time may be shortened by a factor of 2 compared to a case when an interleaving method is not used.

The signal transceiver 320 may acquire raw data necessary to reconstruct an MR image by performing an MRI scan on the object. For example, raw data may be MR signals acquired as RF signals respectively received via a plurality of channel coils in an RF multi-coil (not shown). For example, the signal transceiver 320 may be connected to the RF receiver 38 described with reference to FIG. 1 and receive an MR signal from the RF receiver 38.

According to an exemplary embodiment, the signal transceiver 320 may sequentially acquire a plurality of MR signals respectively corresponding to RF pulses being applied during a TR. In detail, the signal transceiver 320 may acquire 3D data by sampling the MR signals emitted from the object in a 3D K-space.

For example, if the first and third RF pulses are sequentially applied to the object during a TR as described with reference to FIG. 4, the signal transceiver 320 may sequentially acquire MR signals respectively corresponding to the first and third RF pulses. Furthermore, if the second and fourth RF pulses are sequentially applied to the object during a TR, the signal transceiver 320 may sequentially acquire MR signals respectively corresponding to the second and fourth RF pulses.

For example, the signal transceiver 320 may acquire 3D data by sampling sequentially acquired MR signals.

In addition, the acquired MR signals may be provided to an image processor (not shown). The image processor may reconstruct a 3D image of a blood vessel based on the 3D data received from the signal transceiver 320.

According to an exemplary embodiment, the signal transceiver 320 may undersample an MR signal emitted from the object. For example, the image processor 240 may receive undersampled K-space data from the signal transceiver 320 and reconstruct an image of a blood vessel by using extra calibration signals such as in generalized auto-calibrating partial parallel acquisition (GRAPPA) or coil sensitivity maps having additional coil information such as in simultaneous acquisition of spatial harmonics (SMASH). In addition, the image processor may reconstruct an image by using sensitivity encoding (SENSE), parallel imaging with localized sensitivities (PILS), etc.

The image processor may reconstruct an image having a high signal to noise ratio (SNR) and a high spatial resolution by acquiring an MR signal emitted from a large volume according to a 3D TOF method. In particular, the 3D TOF method may be beneficial in acquiring an image of a blood vessel in a region with a high blood flow velocity.

As described above, that the signal transceiver 320 acquires 3D K-space data by sampling an MR signal. However, according to an exemplary embodiment, the signal transceiver 320 may receive an MR signal emitted from the object and the sampling may be performed by the image processor. In other words, the image processor may acquire 3D K-space data by sampling the received MR signal.

Figure 5C:
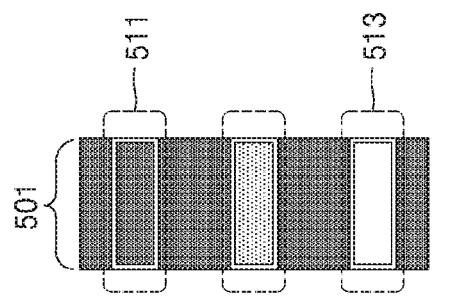
FIGS. 5A, 5B, and 5C are diagrams for explaining a 3D time of flight (TOF) method.
Figure 5B:
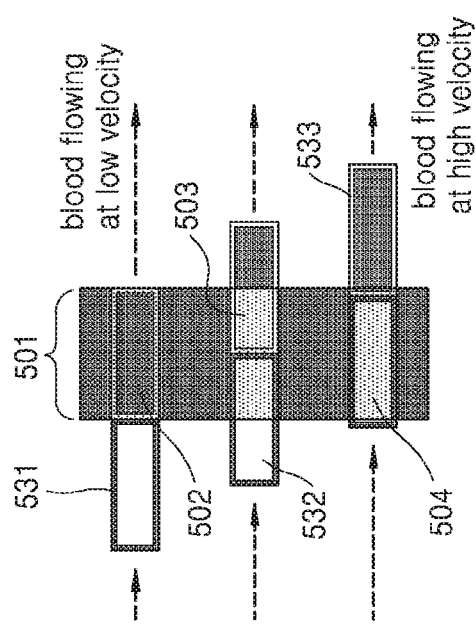
Figure 5A:
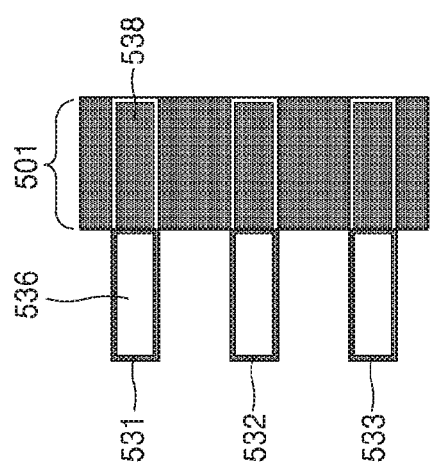

FIGS. 5A through 5C are diagrams for explaining a 3D TOF method. The 3D TOF method is a technique for imaging a blood vessel of an object and may be used to visualize blood flowing into a slab based on flow-related enhancement or in-flow effect. In detail, the RF controller 310 may apply RF pulses having a TR that is shorter than T1 relaxation time, i.e., longitudinal relaxation time of atoms. More specifically, in the 3D TOF method, atoms in static tissue within a slab are excited again when their longitudinal magnetization is not fully recovered (i.e., the atoms in static tissue become saturated), and accordingly an MR signal from flowing blood is stronger than an MR signal from the static tissue. The 3D TOF method may use this difference between strengths of MR signals from blood and the static tissue to reconstruct an image.

For example, referring to FIG. 5A, the RF controller 310 may apply a saturation pulse before applying RF pulses for acquiring data. The saturation pulse may be applied to saturate a static tissue in a slab 501 before an MR signal is acquired from blood.

Furthermore, as shown in FIG. 5A, one or more blood vessels 531, 532, and 533 may be included in the slab 501 and contain blood 536. Furthermore, saturated blood appears dark while unsaturated blood appears bright. For example, the blood 538 in the slab 501 may be saturated and blood 536 that is outside the slab 501 may be unsaturated.

Thereafter, referring to FIG. 5B, the RF controller 310 may repeatedly apply RF pulses corresponding to the slab 501 to the object at intervals of short TR. Thus, a static tissue that has already been saturated remains in the saturated state during repeated application of RF pulses. However, blood 502, 503, and 504 newly flowing into the slab 501 may be unsaturated. In addition, when the RF pulses are applied to the object at intervals of short TR, atoms in the blood 502, 503, and 504 may also become saturated. In detail, since the blood 502 flows through a first blood vessel 531 at low velocity, the blood 502 remains in the first blood vessel 531 within the slab 501 for a long time, so that atoms in the blood 502 may be saturated. On the other hand, since the blood 504 flows through a third blood vessel 533 at high velocity, atoms in the blood 504 newly entering and passing quickly through the third blood vessel 533 may remain unsaturated.

Referring to FIG. 5C, the signal transceiver 320 may acquire MR signals having different strengths according to the degree of saturation of blood. For convenience of explanation, it is assumed in FIG. 5C that a bright region is a region where an MR signal having a greater intensity is acquired. In detail, since the blood 502 flowing through the first blood vessel has been saturated, the signal transceiver 320 does not acquire a signal from the blood 502 flowing in the first blood vessel 531, which is not distinguished from a signal from a static tissue (reference numeral 511). However, since the blood 504 flowing through the third blood vessel 533 remains unsaturated unlike the surrounding saturated static tissue, the signal transceiver 320 may acquire an MR signal from the blood 504 flowing in the third blood vessel 533, which is clearly distinguished from an MR signal from the static tissue (reference numeral 513).

In other words, the strength of an MR signal acquired by the MRI apparatus 300 may vary depending on the degree of saturation of blood, and the degree of saturation of blood may be affected by a blood flow velocity. In this way, the MRI apparatus 300 may be beneficial in obtaining an image of a blood vessel in a region where blood flows at high velocity.

FIG. 6A is a diagram for explaining a method whereby an MRI apparatus operates according to a 3D TOF technique. For example, an MRI apparatus for performing a scan by using a TOF technique may receive an MR signal emitted from an object after applying an RF signal corresponding to one slab during one TR.

Referring to FIG. 6A, the MRI apparatus may apply saturation pulse or pulses 613a to an object in order to saturate static tissues in a slab, prior to applying the RF pulse or pulses.

Thereafter, the MRI apparatus may apply RF pulses 611 corresponding to one slab to the object. In detail, the MRI apparatus may repeatedly apply the RF pulses 611 to the object at intervals of a specific time (i.e., one TR). For example, the number of times that RF pulses corresponding to one slab are repeatedly applied may be determined by a resolution of an MR image or the like.

The MRI apparatus may acquire MR signals respectively corresponding to the RF pulses 611 applied to the object. In detail, the MRI apparatus may acquire MR signals after a lapse of specific time (i.e., one TE) from the time when the RF pulses 611 are respectively applied to the object.

In addition, the TR may include a specific time gap 620 needed after the MRI apparatus acquires an MR signal. This is because it takes a certain amount of time for atoms in blood excited by an RF pulse to recover. A method, performed by the MRI apparatus 300, of shortening a scan time by using the specific time gap 620 will be described in more detail below with reference to FIG. 7A.

Figure 6B:
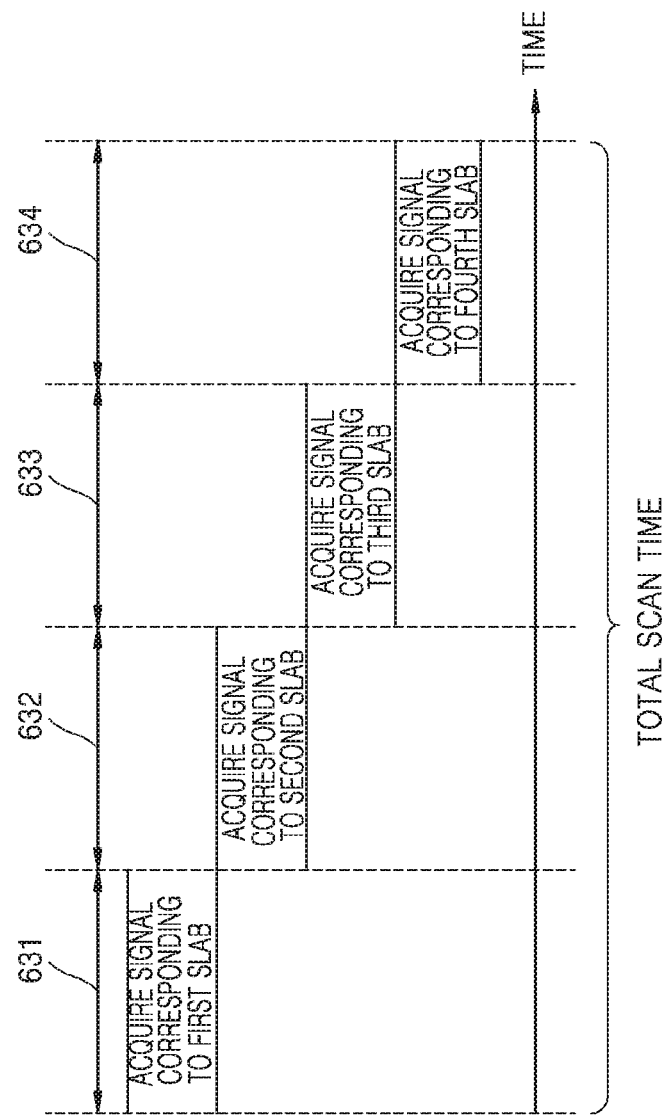
FIG. 6B is diagram for explaining a method of acquiring MR signals from slabs based on a pulse sequence illustrated in FIG. 6A.

FIG. 6B is diagram for explaining a method, performed by an MRI apparatus, of acquiring MR signals from a plurality of slabs based on a pulse sequence 600 illustrated in FIG. 6A. When the pulse sequence 600 of FIG. 6A is used, the MRI apparatus may repeatedly apply RF pulses corresponding to one slab to an object to thereby acquire signals respectively corresponding to the applied RF pulses and then apply RF pulses corresponding to a next slab to the object.

Referring to FIG. 6B, after acquiring MR signals from a first slab 401, the MRI apparatus may sequentially acquire MR signals respectively from second through fourth slabs 402 through 404. Thus, a total scan time may be the sum of scan times 631, 632, 633, and 634 required to acquire the MR signals respectively from the first through fourth slabs 401 through 404. Thus, as the number of slabs increases, the total scan time may increase in proportion to the number of slabs.

Alternatively, the MRI apparatus may apply RF pulses respectively corresponding to different slabs during each TR and acquire MR signals respectively corresponding to the applied RF pulses. However, even in this case, the total scan time is not reduced.

FIG. 7A is another diagram for explaining a method of operating the MRI apparatus 300 according to a 3D TOF technique according to an exemplary embodiment.

Referring to FIG. 7A, the RF controller 310 may apply first and second RF pulses 711 and 712 respectively corresponding to grouped slabs among a plurality of slabs to an object during one TR.

In detail, as described with reference to FIG. 6A, the RF controller 310 may apply the first and second RF pulses 711 and 712 respectively corresponding to grouped slabs during one TR to the object by using a specific time gap 620. For example, the RF controller 310 may sequentially apply the first RF pulse 711 corresponding to a first slab 401 that is one of the grouped slabs and then the second RF pulse 712 corresponding to a third slab 403 that is another slab grouped with the first slab 401, during the same TR.

The TRs shown in FIGS. 6A and 7A may be equal to each other or different. Furthermore, although FIG. 7A shows that a pulse sequence 700 does not include the saturation pulses (613a of FIG. 6A), a pulse sequence 700 may further include the saturation pulses 613a in addition to the pulses illustrated in FIG. 7A.

Figure 7B:
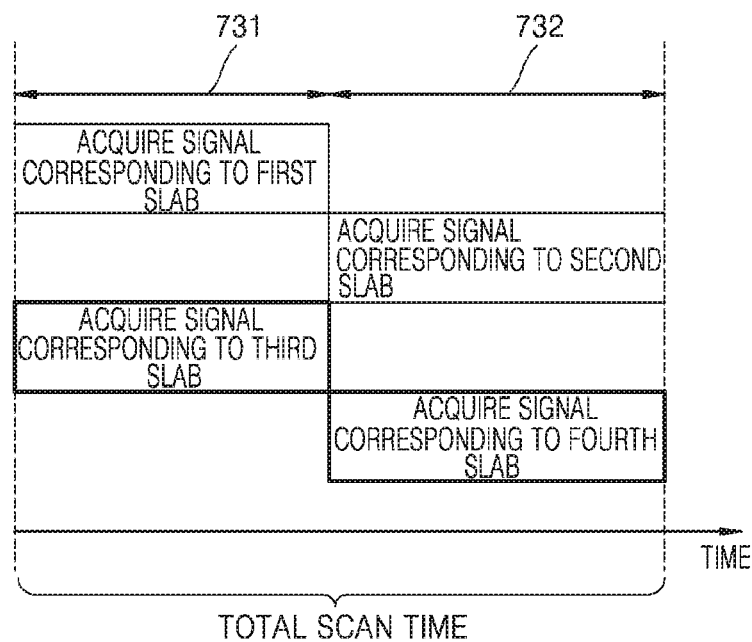
FIG. 7B is a diagram for explaining a method of acquiring MR signals from slabs based on a pulse sequence illustrated in FIG. 7A.

FIG. 7B is a diagram for explaining a method, performed by the MRI apparatus 300, of acquiring MR signals from a plurality of slabs based on the pulse sequence 700 illustrated in FIG. 7A. When the pulse sequence 700 of FIG. 7A is used, the MRI apparatus 300 may repeatedly apply RF pulses corresponding to a plurality of slabs to the object during one TR to thereby acquire MR signals respectively corresponding to the applied RF pulses.

Referring to FIG. 7B, after acquiring MR signals from first and third slabs 401 and 403, the MRI apparatus 300 may acquire MR signals from second and fourth slabs 402 and 404. Furthermore, a scan time 731 required to acquire MR signals respectively from the first and third slabs 401 and 403 may be substantially similar to the scan time 631 required to acquire MR signals from a single first slab of FIG. 6B.

Thus, a total scan time needed to acquire the MR signals respectively corresponding to the first through fourth slabs 401 through 404 may be reduced by a factor of the number of grouped slabs (e.g., by a factor of 2), as compared to the total scan time shown in FIG. 6B.

Figure 8:
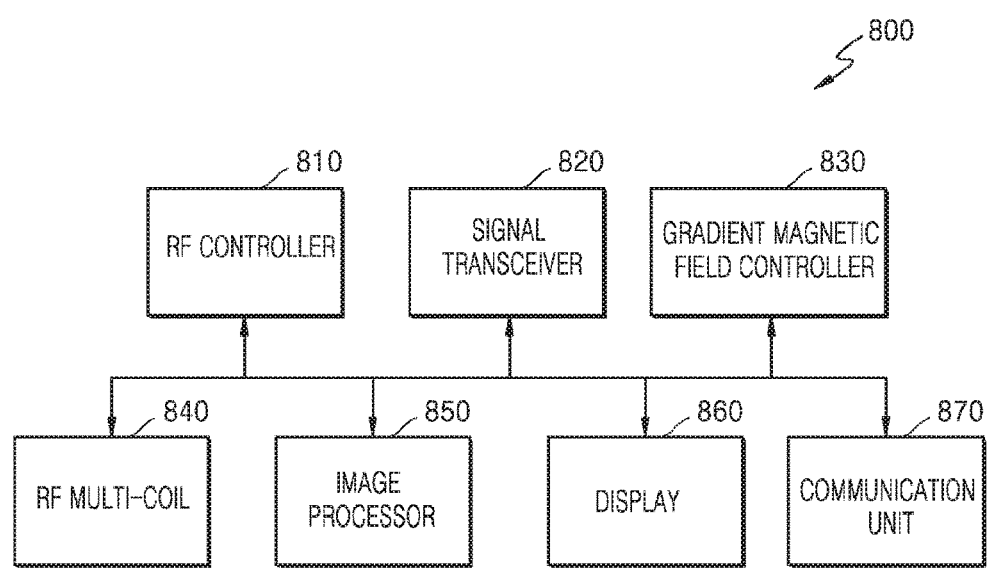
FIG. 8 is a block diagram of an MRI apparatus according to an exemplary embodiment.

FIG. 8 is a block diagram of an MRI apparatus 800 according to an exemplary embodiment.

Referring to FIG. 8, in the MRI apparatus 800 according to the exemplary embodiment, an RF controller 810 and a signal transceiver 820 may respectively correspond to the RF controller 310 and the signal transceiver 320 described with reference to FIG. 3. Thus, descriptions of the MRI apparatus 800 that are already provided above with respect to FIG. 3 will be omitted here.

The MRI apparatus 800 may further include at least one of a gradient controller 830, an RF multi-coil 840, an image processor 850, a display 860, and a communication unit 870.

The gradient magnetic field controller 830, the RF multi-coil 840, the image processor 850, the display 860, and the communication unit 870 may respectively correspond to the gradient magnetic field controller 54, the RF coil 26, the image processor 62, the output unit 64, and the communicator 70 described with reference to FIGS. 1 and 2. Thus, descriptions that are already provided above with reference to FIGS. 1 and 2 will be omitted below.

The RF controller 810 may sequentially apply a plurality of RF pulses including saturation pulses to an object by using a 3D TOF method. For example, the RF controller 810 may apply a plurality of RF pulses to the object during a TR, based on an interleaving method.

In detail, the RF controller 810 may apply RF pulses respectively corresponding to grouped slabs among a plurality of slabs to the object during one TR. If the plurality of slabs include first through fourth slabs, the grouped slabs may be the first and third slabs or the second and fourth slabs, which are not adjacent to each other. However, if the plurality of slabs include first and second slabs, the grouped slabs may be the first and second slabs.

According to an exemplary embodiment, the RF controller 810 may adjust flip angles of RF pulses respectively corresponding to grouped slabs based on a direction of blood flow. In detail, if the plurality of slabs include first through fourth slabs, the RF controller 810 may adjust, when blood first flows into the first slab, flip angles of RF pulses respectively corresponding to the grouped first and third slabs so that the flip angles are progressively increased. A method of adjusting flip angles of RF pulses, which is performed by the RF controller 810, will be described in more detail below with reference to FIGS. 9A, 9B, 10, and 11.

For example, the RF controller 810 may adjust the directionality of transmission and reception of an RF pulse and an MR signal. For example, the RF controller 810 may control an RF signal to be transmitted to the object via the RF multi-coil 840 in a transmission mode and an MR signal to be received from the object via the RF multi-coil 840 in a reception mode. The RF controller 810 may generate a control signal for controlling transmission of an RF pulse and reception of an MR signal.

The gradient magnetic field controller 830 may correspond to the gradient magnetic field controller 56 described with reference to FIG. 1. The gradient magnetic field controller 830 may apply a gradient pulse to form magnetic field gradients (hereinafter, referred to as 'gradients') respectively corresponding to a plurality of slabs to the object. For example, the gradient magnetic field controller 830 may control the gradient coil (24 of FIG. 1) in order to generate spatial encoding gradients. For example, the spatial encoding gradients may include gradients in X-, Y-, and Z-axis directions. In detail, the gradient magnetic field controller 830 may apply a pulse signal to X- Y- and Z-coils for generating gradients in the X-, Y-, and Z-axis directions that are perpendicular to one another. In response to the applied pulse signal, the gradients in the X-, Y-, and Z-axis directions may be generated. The gradient coil 24 that has received the pulse signal from the gradient magnetic field controller 830 may provide location information of each of regions of the object by inducing different resonant frequencies according to the regions of the object.

For example, the gradients in the X-, Y-, and Z-axis directions may respectively correspond to a frequency encoding gradient Gfrequency, a phase encoding gradient Gphase, and a slice selection gradient Gslice shown in FIGS. 6A and 7A. According to an exemplary embodiment, a gradient in a frequency encoding direction may correspond to a gradient in a Y-axis direction of K-space.

The RF multi-coil 840 may include a channel. For example, the RF multi-coil 840 may include first through n-th channels, each of which may receive an MR signal that is an RF signal.

For example, the RF multi-coil 840 may include a channel via which an RF pulse is applied to the object and an MR signal emitted from a nuclear spin of the object is received. The signal transceiver 820 may acquire an MR signal detected by the channel.

The signal transceiver 820 may sample the MR signal acquired via the channel in the RF multi-coil 840. In detail, the signal transceiver 820 may generate 3D K-space data by sampling the MR signal acquired via the RF multi-coil 840. The signal transceiver 820 may provide the generated 3D K-space data to the image processor 850.

In detail, after RF pulses respectively corresponding to grouped slabs are applied to the object during each TR, the signal transceiver 820 may acquire MR signals respectively corresponding to the applied RF pulses.

For example, the signal transceiver 820 may acquire MR signals respectively corresponding to RF pulses having adjusted flip angles. Thus, the signal transceiver 820 may acquire, from blood, MR signals whose intensities (strengths) are kept constant at a specific level. A method, performed by the signal transceiver 820, of acquiring an MR signal whose intensity is kept constant will be described in detail below with reference to FIG. 12.

The image processor 850 may reconstruct an MR image from the 3D K-space data provided by the signal transceiver 820.

The display 860 displays a screen. In detail, the display 860 may display a predetermined screen via the above-described various types of displays including a CRT display, a LCD, a PDP, an OLED display, a FED, a light emitting diode (LED) display, a VFD, a DLP display, a flat panel display, a 3D display, and a transparent display. According to an exemplary embodiment, the display 860 may display a reconstructed MR image.

FIGS. 9A and 9B are diagrams for explaining a direction of blood flow and a saturated state of atoms in blood.

The MRI apparatus 800 may reconstruct an image of a blood vessel based on MR signals acquired from a plurality of slabs, i.e., first through fourth slabs 901 through 904. In detail, the MRI apparatus 800 may reconstruct an image by acquiring high intensity MR signals emitted from blood 912 and 914 flowing through blood vessels (i.e., static tissues 911 and 913). Thus, it may be desirable to keep atoms in the blood 912 and 914 unsaturated, wherein the blood 912 and 914 is flowing through the blood vessels in the first through fourth slabs 901 through 904.

Referring to FIGS. 9A and 9B, according to an exemplary embodiment, the MRI apparatus 800 may sequentially apply RF pulses respectively corresponding to the grouped first and third slabs 901 and 903 to an object during each TR. As shown in FIG. 9A, as atoms in the blood 912 entering the first slab 901 move from the first slab 901 to the third slab 903, the atoms in the blood 912 may be progressively saturated. Thus, the blood 912 that reaches the third slab 903 may emit an MR signal having a lower intensity than that of an MR signal emitted when it is located in the first slab 901.

Alternatively, as shown in FIG. 9B, the blood 914 may first flow into the fourth slab 904. As the blood 914 moves from the third slab 903 to the first slab 901, the atoms may be progressively saturated so that the blood 914 that reaches the first slab 901 emits a signal having a lower intensity than when it is located in the third slab 903.

Thus, the RF controller 810 may adjust flip angles of RF pulses respectively corresponding to some of the interleaved slabs (i.e., the first and third slabs 901 and 903) in order to keep constant intensities of MR signals acquired from blood. A method, performed by the RF controller 810, of adjusting flip angles of RF pulses will now be described in more detail.

Figure 10:
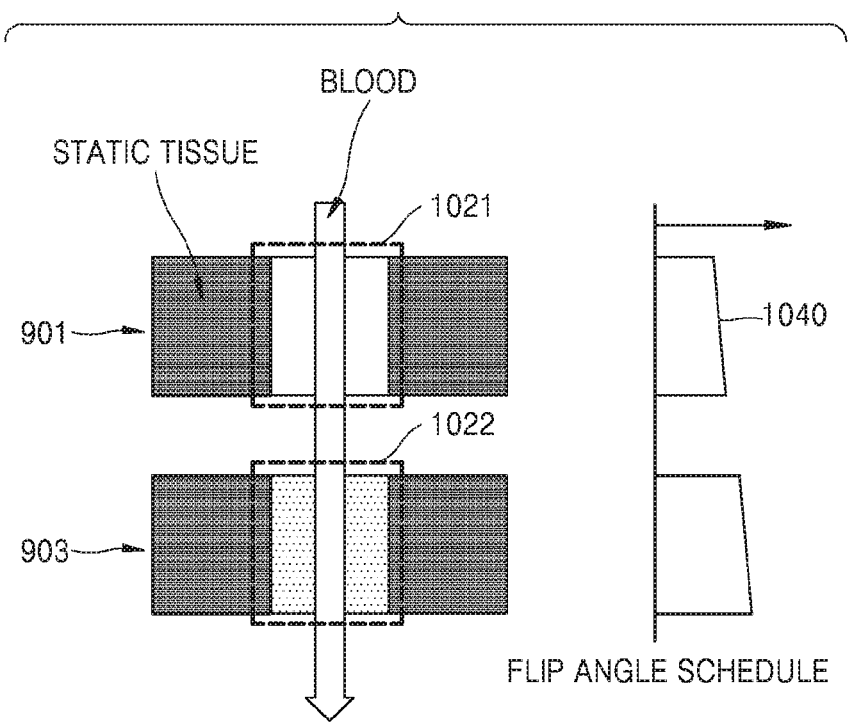
FIG. 10 is a diagram for explaining a method of generating a flip angle schedule for adjusting flip angles of RF pulses.

FIG. 10 is a diagram for explaining a method, performed by the RF controller 810, of generating a flip angle schedule for adjusting flip angles of RF pulses.

Referring to FIG. 10, the RF controller 810 may adjust flip angles of RF pulses which are applied to an object during one TR and respectively correspond to grouped slabs (e.g., the first and third slabs 901 and 903 of FIG. 9). In detail, the RF controller 810 may generate a flip angle schedule 1040 for RF pulses to be applied to the object during each TR. Here, the flip angle schedule 1040 may be a graph determined based on a volume of a slab and minimum and maximum values of flip angles.

For example, the blood 1020 may first enter the first slab 901 and flow towards the third slab 903. For example, the RF controller 810 may generate, based on a direction of blood flow, a flip angle schedule that linearly increases from the first slab 901 towards the third slab 903. An intensity of an MR signal emitted by atoms in the blood 1020 may vary according to a magnitude of a flip angle of a corresponding RF pulse. In detail, as a flip angle of an RF pulse increases, atoms may emit an MR signal having a higher intensity. As atoms excited by an RF pulse approach a saturated state, the atoms may emit an MR signal having a lower intensity.

Thus, since unsaturated blood 1021 flows in the first slab 901, the RF controller 810 may adjust RF pulses corresponding to the first slab 901 to have small flip angles. For example, the RF controller 801 may adjust RF pulses corresponding to the third slab 903, through which near-saturated blood 1022 flows, to have relatively large flip angles. By performing such adjustments, the RF controller 810 may control intensities of MR signals emitted by the blood 1021, 1022 to be constant.

In detail, the RF controller 810 may determine a slope of the flip angle schedule 1040 based on a blood flow velocity. For example, if it takes 10 TRs for the blood 1020 to pass through the first and third slabs 901 and 903, the flip angle schedule 1040 may be a linear graph having an 80% slope. As another example, if the blood 1020 has all passed through the first and third slabs 901 and 903 during one TR, the flip angle schedule may be a linear graph having a 0% slope.

While it is described with reference to FIG. 10 that the RF controller 810 generates a flip angle schedule for the blood 901 entering the first slab 901, the RF controller 810 may generate a flip angle schedule for blood entering the third slab 903. For example, if the blood first flows into the third slab 903, the RF controller 810 may generate a flip angle schedule that linearly decreases from the first slab 901 towards the third slab 903.

Furthermore, although it is described with reference to FIG. 10 that a flip angle schedule linearly increases (or decreases), exemplary embodiments are not limited thereto. According to an exemplary embodiment, the flip angle schedule may increase (or decrease) exponentially.

Figure 11:
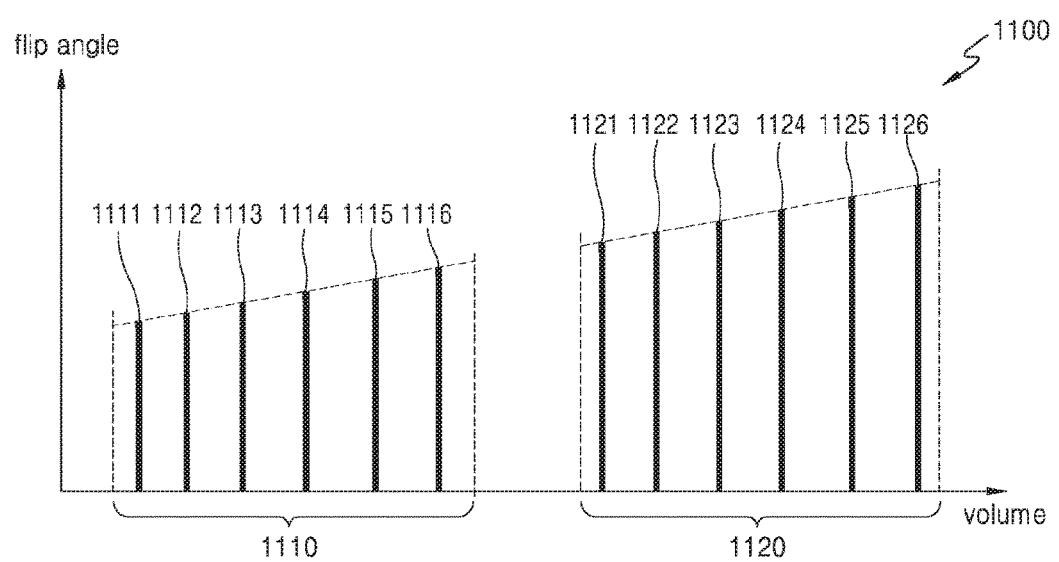
FIG. 11 is a diagram for explaining a method of determining flip angles of RF pulses being applied to an object during each repetition time (TR) based on a flip angle schedule.

FIG. 11 is a diagram of a method, performed by the RF controller 810, of determining flip angles of RF pulses being applied to the object during each TR based on a flip angle schedule.

Referring to FIG. 11, the RF controller 810 may determine, based on a flip angle schedule 1100, flip angles of RF pulses respectively corresponding to grouped slabs (e.g., the first and third slabs 901 and 903 of FIG. 9). For convenience of explanation, it is assumed that the RF controller 810 repeatedly applies RF pulses six times for each slab (i.e., during 6 TRs) in order to obtain an MR image.

In detail, the RF controller 810 may select first through sixth points 1111, 1112, 1113, 1114, 1115, and 1116 from a first interval 1110 corresponding to the first slab 901. For example, the RF controller 810 may select first through sixth points 1121, 1122, 1123, 1124, 1125, and 1126 from a second interval 1120 corresponding to the third slab 903.

The RF controller 810 may sequentially apply RF pulses respectively corresponding to the first and third slabs 901 and 903 during one TR. Thus, the RF controller 810 may sequentially apply to the object an RF pulse having a flip angle corresponding to the first point 1111 in the first interval 1110 and an RF pulse having a flip angle corresponding to the first point 1121 in the second interval 1120 during a first TR. For example, the RF controller 810 may sequentially apply to the object an RF pulse having a flip angle corresponding to the second point 1112 in the first interval 1110 and an RF pulse having a flip angle corresponding to the second point 1122 in the second interval 1120 during a second TR. In this way, the RF controller 810 may sequentially apply to the object RF pulses having flip angles respectively corresponding to points in the first and second intervals 1110 and 1120 during each TR.

Although the method of applying RF pulses respectively corresponding to some of the first through fourth slabs 901 through 904 (i.e., the first and third slabs 901 and 903) is described above, the RF controller 810 may also apply RF pulses respectively to the other slabs by using the same method.

Figure 12:
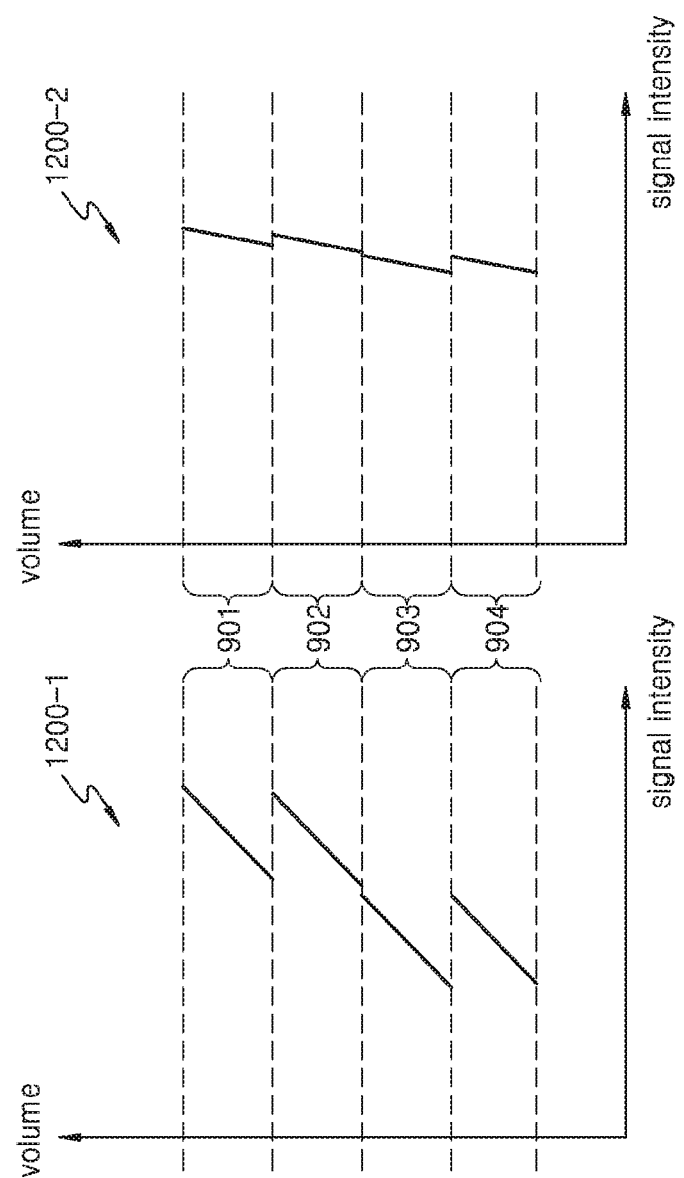
FIG. 12 is a diagram for explaining a method of acquiring MR signals.

FIG. 12 is a diagram for explaining a method, performed by the signal transceiver 820, of acquiring MR signals. The signal transceiver 820 may sequentially acquire MRF signals respectively corresponding to RF pulses applied to the object during a TR. In detail, the signal transceiver 820 may sequentially acquire MR signals during TR, the MR signals respectively corresponding to grouped first and third slabs 1201 and 1203 among first through fourth slabs 1201 through 1204. Thereafter, the signal transceiver 820 may sequentially acquire MR signals respectively corresponding to the grouped second and fourth slabs 1202 and 1204 during TR.

In FIG. 12, a graph 1200-1 shows intensities of MR signals acquired by the signal transceiver 820 when the RF controller 810 does not adjust flip angles of RF pulses. Furthermore, a graph 1200-2 shows intensities of MR signals acquired by the signal transceiver 820 after the RF controller 810 adjusts flip angles of RF pulses. As seen on a graph 1200-1, intensities of the MR signals respectively corresponding to the grouped first and third slabs 1201 and 1203 decrease linearly. This may be because, as described above, atoms in blood that emit the MR signals are progressively saturated according to the direction and velocity of blood flow. On the other hand, as seen on a graph 1200-2, the intensities of MR signals respectively corresponding to the grouped first and third slabs 1201 and 1203 may be kept constant. This may be because flip angles of RF pulses applied to the object have been adjusted according to the direction and velocity of blood flow.

The signal transceiver 820 may acquire 3D K-space data by sampling MR signals whose intensities are kept constant at a specific level. For example, the image processor 850 may reconstruct, based on the 3D K-space data provided by the signal transceiver 820, a 3D MR image having an averaged contrast between blood vessels and static tissue.

Figure 13:
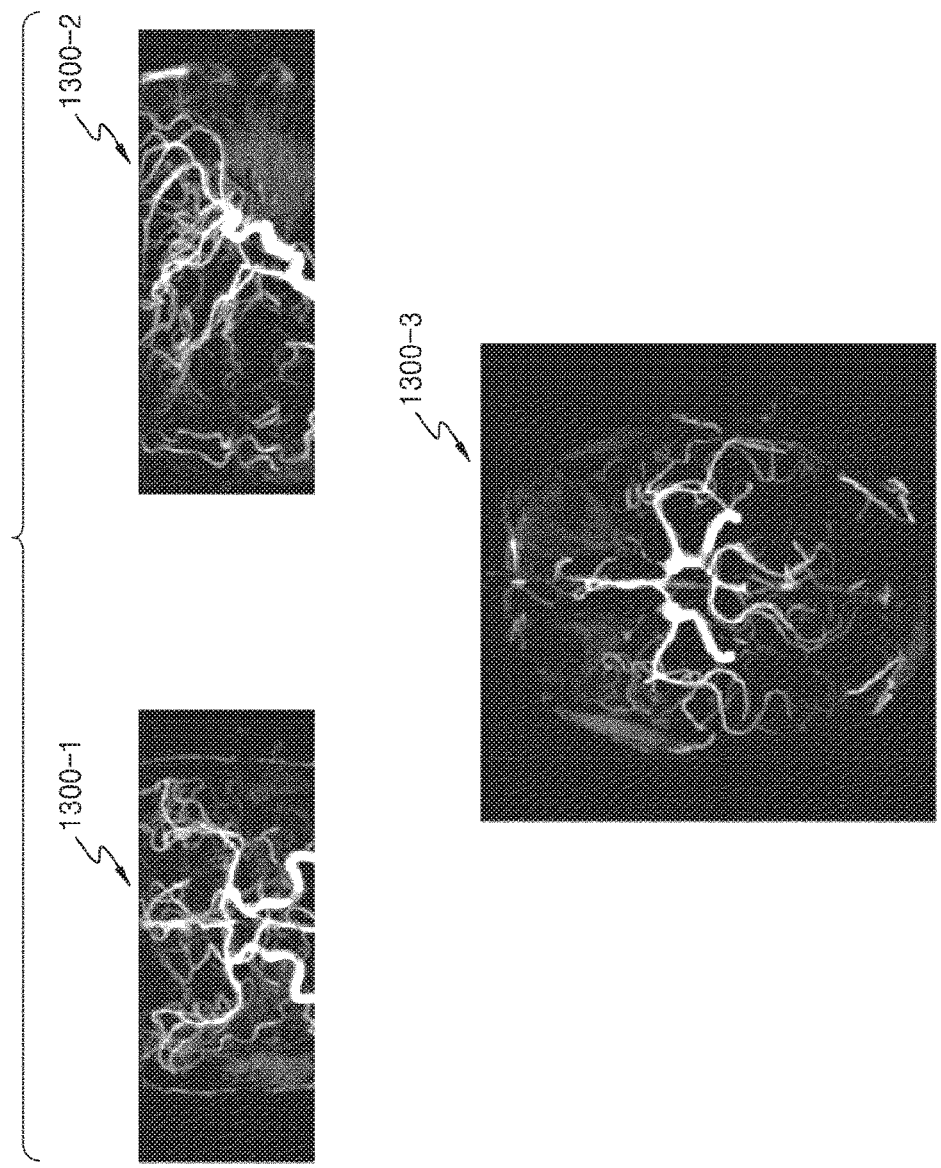
FIG. 13 illustrates an example of a 3D MR image reconstructed by an MRI apparatus.

FIG. 13 illustrates an example of a 3D MR image reconstructed by the MRI apparatus 800.

Referring to FIG. 13, the image processor 850 may reconstruct a 3D MR image based on 3D K-space data obtained via sampling or undersampling. In detail, the image processor 850 may reconstruct 3D MR images respectively corresponding to a plurality of slabs and reconstruct a single 3D MR image by synthesizing the reconstructed 3D MR images.

In detail, images 1300-1 and 1300-2 show 3D MR images respectively corresponding to a plurality of slabs, for example, grouped first and third slabs and grouped second and fourth slabs, respectively. An image 1300-3 shows one 3D MR image corresponding to the plurality of slabs. As seen on the images 1300-1 through 1300-3, the reconstructed 3D MR image may be an image with an averaged contrast between blood vessels and static tissue.

Figure 14:
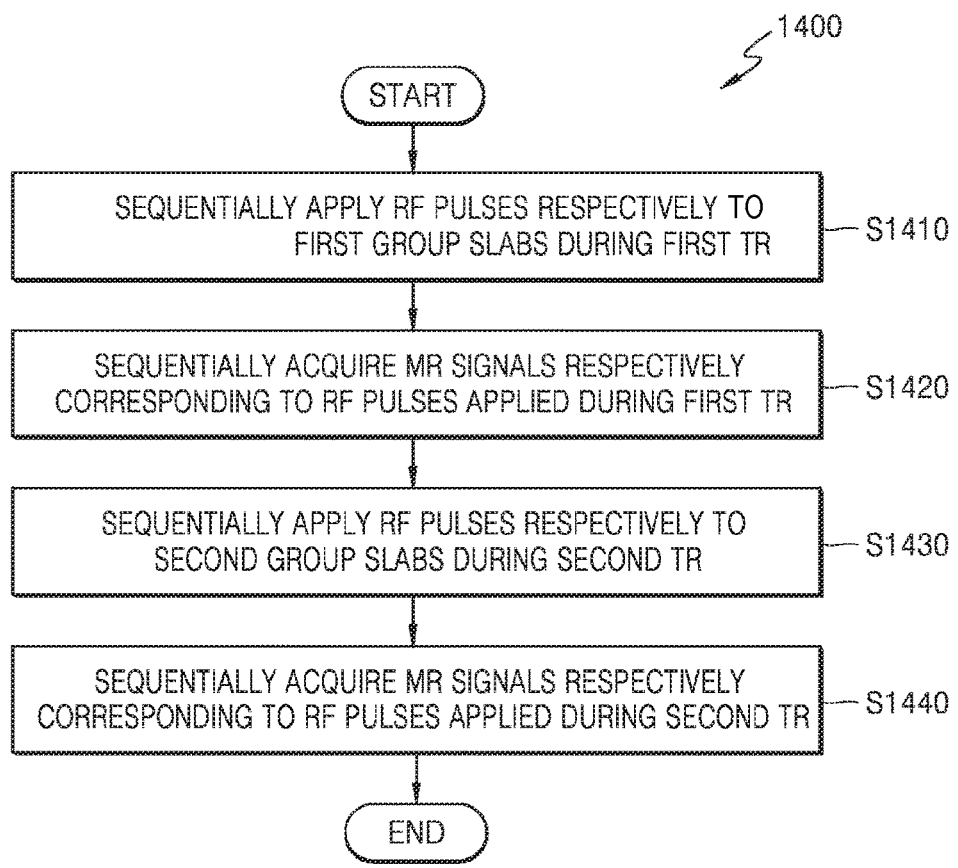
FIG. 14 is a flowchart of a method of scanning a blood vessel according to an exemplary embodiment.

FIG. 14 is a flowchart of a method 1400 of scanning a blood vessel according to an exemplary embodiment. The method 1400 according to the exemplary embodiment may include the same operations and functionalities as performed and implemented_by the MRI apparatus 300 and/or 800 according to the exemplary embodiments described above with reference to FIGS. 1 through 13. Thus, descriptions that are already provided above will be omitted.

Referring to FIG. 14, in the method 1400, a plurality of RF pulses may be sequentially applied respectively to a plurality of first group slabs among a plurality of slabs during a first TR (operation S1410). Since operation S1410 may be substantially the same as that of the RF controller 310, a detailed description thereof will be omitted here.

According to an exemplary embodiment, in the method 1400, before operation S1410, saturation RF pulses may be applied to an object. A saturation RF pulse may be applied to saturate a static tissue in order to scan a blood vessel.

According to the method 1400, a region being scanned may be divided into a plurality of slabs, and the RF pulses and gradient pulses respectively corresponding to the plurality of slabs may be applied by using a TOF method. In detail, in the method 1400, the plurality of slabs may be grouped into at least one group, each group including a plurality of slabs disposed with gaps from one another. For example, if the plurality of slabs include sequential first through fourth slabs, the plurality of slabs may be grouped into a first group including the first and third slabs and a second group including the second and fourth slabs. For example, interleaving may mean that the MRI apparatus 300 may sequentially apply different RF pulses respectively corresponding to different slabs to the object during one TR.

In the method 1400, a plurality of MR signals respectively corresponding to the plurality of RF pulses applied during the first TR may be sequentially acquired (operation S1420). Since operation S1420 may be substantially the same as that of the signal transceiver 320, a detailed description thereof will be omitted here.

Furthermore, in the method 1400, a plurality of RF pulses may be sequentially applied respectively to a plurality of second group slabs (e.g., second and fourth slabs) among the plurality of slabs during a second TR (operation S1430). Then, a plurality of MR signals respectively corresponding to the plurality of RF pulses applied during the second TR may be sequentially acquired (operation S1440). Since operations S1430 and S1440 are respectively similar to operations S1410 and S1420, detailed descriptions thereof will be omitted here. In addition, the first and second TRs may be equal or similar to each other (e.g., 20 ms).

According to the method 1400, by applying RF pulses respectively corresponding to a plurality of interleaved slabs and acquiring MR signals respectively corresponding to the applied RF pulses, it is possible to reduce a scan time required to scan a blood vessel.

Figure 15:
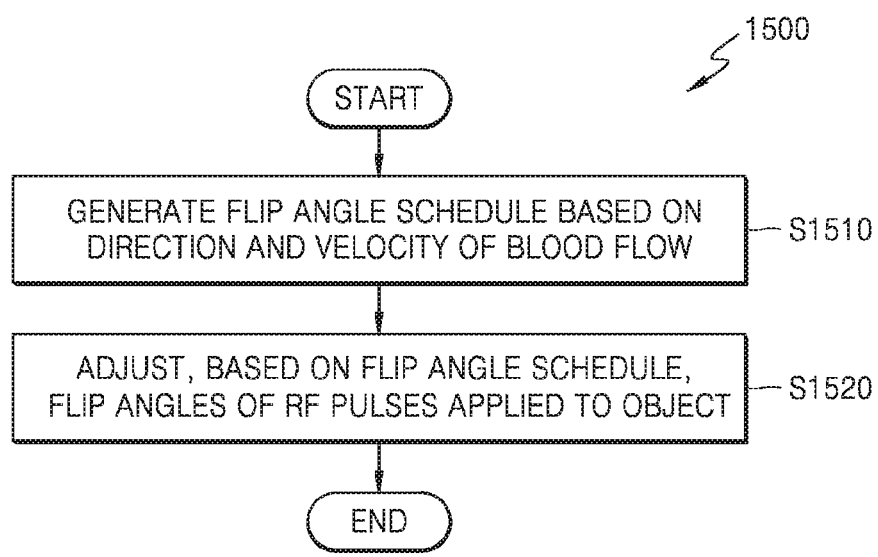
FIG. 15 is a detailed flowchart of a method of adjusting flip angles of RF pulses in scanning a blood vessel, according to an exemplary embodiment.

FIG. 15 is a detailed flowchart of a method 1500 of adjusting flip angles of RF pulses in a method of scanning a blood vessel, according to an exemplary embodiment. The method 1500 according to the exemplary embodiment may include the same operations and functions as performed and implemented by the MRI apparatuses 300 and/or 800 described above with reference to FIGS. 1 through 13. Thus, descriptions that are already provided above will be omitted.

Referring to FIG. 15, in the method 1500, a flip angle schedule may be generated based on the direction and velocity of blood flow (operation S1510). Since operation S1510 may be substantially the same as that of the RF controller 810, a detailed description thereof will be omitted here.

In the method 1500, flip angles of RF pulses applied to an object may be adjusted based on the generated flip angle schedule (operation S1520). Since operation S1520 may be substantially the same as that of the signal transceiver 820, a detailed description thereof will be omitted here.

The method 1500 may reduce the scan time and may also provide an MR image having an averaged contrast between blood vessels and static tissue by adjusting flip angles of RF pulses applied to the object, as described above.

The exemplary embodiments can be written as computer programs and can be implemented in general-use digital computers that execute the programs using a non-transitory computer-readable recording medium.

Furthermore, when a processor of a computer needs to communicate with any other computers or servers at remote locations in order to execute the above-mentioned functions, the processor may further include information about how the processor of the computer can communicate with any other computers or servers at remote locations by using a communication module (e.g., wired and/or wireless communication module) of the computer, information about which information or media the processor is to transmit or receive during the communication.

Furthermore, a functional program for implementing an exemplary embodiment, a code and a code segment associated therewith, and the like may be easily inferred or modified by those skilled in the art in consideration of a system environment of the computer which reads the recording medium and executes the program.

Examples of the non-transitory computer-readable recording medium having recorded the above-described programs thereon include a ROM, a RAM, a CD-ROM, a magnetic tape, a floppy disk, an optical media storage device, etc.

For example, the non-transitory computer-readable recording medium may also be distributed over network-coupled computer systems so that the computer-readable codes are stored and executed in a distributed fashion. For example, at least one computer among a plurality of distributed computers may execute a part of the above-described functions and transmit a result of execution to at least one of the other distributed computers, and the computer receiving the result may also execute a part of the above-described functions and provide a result of execution to the rest of distributed computers.

Although it is described that all components in the exemplary embodiments of the present inventive concept are combined as one component or are combined to be operated, exemplary embodiments are not limited thereto. In other words, all the components may be selectively combined into at least one component to be operated without departing from the scope of the present invention. Furthermore, although each of all the components may be implemented using one independent hardware device, some or all of the respective components may be selectively combined with one another and be implemented as a computer program having a program module for performing functions of some or all of the components combined with one another in one or a plurality of hardware devices. Codes and code segments configuring the computer program may be readily inferred by those of ordinary skill in the art to which the present invention pertains. The computer programs may be stored in non-transitory computer-readable media and be read and executed by the computer, thereby implementing the exemplary embodiments of the present inventive concept. Examples of storage media having computer programs stored therein may include magnetic recording media, optical recording media, and the like.

Furthermore, it will be understood that the terms "includes", "comprises", "including", and/or "comprising" used in this specification, unless there is a particular description contrary thereto, specify the presence of stated elements and/or components, but do not preclude the presence or addition of one or more elements and/or components thereof. Unless defined otherwise, all terms including technical or scientific terms used herein have the same meaning as commonly understood by those of ordinary skill in the art to which exemplary embodiments belong. General terms such as terms defined in dictionaries should also be interpreted as being consistent with their meaning in the context of the relevant art and will not be interpreted in an idealized or overly formal sense unless expressly defined herein.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A magnetic resonance imaging (MRI) method of scanning a blood vessel, the method comprising:
    sequentially applying, according to a time-of-flight (TOF) method, radio frequency (RF) pulses respectively to first grouped slabs, among interleaved slabs, during a first repetition time (TR);
    sequentially acquiring MR signals respectively corresponding to the RF pulses applied during the first TR;
    sequentially applying, according to the TOF method, the RF pulses respectively to second grouped slabs, among the interleaved slabs, during a second TR;
    sequentially acquiring the MR signals respectively corresponding to the RF pulses applied during the second TR; and
    reconstructing an MR image of the blood vessel based on the MR signals acquired during the first TR and the second TR.

2. The method of claim 1, wherein the interleaved slabs comprise first, second, third, and fourth slabs that are sequentially arranged in this order,
    the first grouped slabs comprise the first and third slabs, and
    the second grouped slabs comprise the second and fourth slabs.

3. The method of claim 2, wherein the sequentially applying the RF pulses to the first grouped slabs comprises:
    generating a first flip angle schedule for the RF pulses applied to the first and third slabs based on at least one among a direction of a blood flow and a velocity of the blood flow; and
    adjusting a flip angle of a first RF pulse applied to the first slab and a flip angle of a third RF pulse applied to the third slab based on the generated first flip angle schedule.

4. The method of claim 3, wherein the generating the first flip angle schedule comprises:
    generating the first flip angle schedule having an increasing slope in response to a blood flowing into the first slab before flowing into the third slab; and
    generating the first flip angle schedule having a decreasing slope in response to the blood flowing into the third slab before flowing into the first slab.

5. The method of claim 2, wherein the sequentially applying the RF pulses to the second grouped slabs comprises:
    generating a second flip angle schedule for the RF pulses applied to the second and fourth slabs based on at least one among a direction of a blood flow and a velocity of the blood flow; and
    adjusting a flip angle of a second RF pulse applied to the second slab and a flip angle of a fourth RF pulse applied to the fourth slab based on the generated second flip angle schedule.

6. The method of claim 5, wherein the generating the second flip angle schedule comprises:
    generating the second flip angle schedule having an increasing slope in response to a blood flowing into the second slab before flowing into the fourth slab; and
    generating the second flip angle schedule having a decreasing slope in response to the blood flowing into the fourth slab before flowing into the second slab.

7. The method of claim 1, further comprising applying saturation pulses prior to the applying the RF pulses.

8. The method of claim 1, wherein the RF pulses are applied based on a three-dimensional (3D) TOF method.

9. The method of claim 1, further comprising reconstructing a three-dimensional (3D) image of the blood vessel based on the MR signals acquired during the first TR and the second TR.

10. A magnetic resonance imaging (MRI) apparatus comprising:
    a radio frequency (RF) controller configured to sequentially apply, based on a time-of-flight (TOF) method, RF pulses respectively to first grouped slabs, among interleaved slabs, during a first repetition time (TR); and
    a signal transceiver configured to sequentially acquire MR signals respectively corresponding to the RF pulses applied during the first TR,
    wherein the RF controller is further configured to sequentially apply, based on the TOF method, the RF pulses respectively to second grouped slabs, among the interleaved slabs, during a second TR, and
    the signal transceiver is further configured to sequentially acquire signals respectively corresponding to the RF pulses applied during the second TR.

11. The MRI apparatus of claim 10, wherein the interleaved slabs comprise first, second, third, and fourth slabs that are sequentially arranged in this order,
    the first grouped slabs comprise the first and third slabs, and
    the second grouped slabs comprise the second and fourth slabs.

12. The MRI apparatus of claim 11, wherein the RF controller is further configured to generate a first flip angle schedule for the RF pulses being applied to the first and third slabs based on at least one among a direction of a blood flow and a velocity of the blood flow, and to adjust a flip angle of a first RF pulse being applied to the first slab and a flip angle of a third RF pulse being applied to the third slab based on the generated first flip angle schedule.

13. The MRI apparatus of claim 12, wherein the RF controller is further configured to generate the first flip angle schedule having an increasing slope in response to a blood flowing into the first slab before flowing into the third slab, and to generate the first flip angle schedule having a decreasing slope in response to the blood flowing into the third slab before flowing into the first slab.

14. The MRI apparatus of claim 11, wherein the RF controller is further configured to generate a second flip angle schedule for the RF pulses being applied to the second and fourth slabs based on at least one among a direction of a blood flow and a velocity of the blood flow, and to adjust a flip angle of a second RF pulse being applied to the second slab and a flip angle of a fourth RF pulse being applied to the fourth slab based on the generated second flip angle schedule.

15. The MRI apparatus of claim 14, wherein the RF controller is further configured to generate the second flip angle schedule having an increasing slope in response to the blood flowing into the second slab before flowing into the fourth slab, and to generate the second flip angle schedule having a decreasing slope in response to the blood flowing into the fourth slab before flowing into the second slab.

16. The MRI apparatus of claim 10, wherein the RF controller is configured to apply saturation pulses prior to an application of the RF pulses.

17. The MRI apparatus of claim 10, wherein the RF controller is configured to apply the RF pulses based on a three-dimensional (3D) TOF method.

18. The MRI apparatus of claim 10, further comprising:
an image processor configured to reconstruct a three-dimensional (3D) image of a blood vessel based on the MR signals acquired during the first TR and the second TR.

19. A non-transitory computer-readable recording medium having recorded thereon a program which, when executed by a computer, causes the computer to perform the method of claim 1.

* * * * *